United States Patent
Gallagher et al.

(10) Patent No.: US 6,556,923 B2
(45) Date of Patent: *Apr. 29, 2003

(54) SOFTWARE FOR HIGH THROUGHPUT MICROFLUIDIC SYSTEMS

(75) Inventors: Steven J. Gallagher, Palo Alto, CA (US); J. Wallace Parce, Palo Alto, CA (US)

(73) Assignee: Caliper Technologies Corp., Mountain View, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/491,691

(22) Filed: Jan. 26, 2000

(65) Prior Publication Data

US 2002/0052696 A1 May 2, 2002

(51) Int. Cl.[7] .............................................. G01N 27/26
(52) U.S. Cl. ............................. 702/23; 702/22; 702/30; 702/32; 422/63; 422/68.1
(58) Field of Search ........................... 702/23, 19, 22, 702/27, 30–32, 45, 50, 55, 100, 183, FOR 115–FOR 119, FOR 134, FOR 170, FOR 171; 700/266; 436/806–808, 149, 150, 73, 514; 435/46, 287.1–287.3, 288.4, 288.5, 973; 137/551, 597; 204/450, 451, 453, 459, 600–604, 400, 406, 407, 409, 411, 412, 403; 422/99, 100, 68.1, 50, 56–58, 70, 60–63, 67, 81, 82, 82.01, 102; 356/344

(56) References Cited

U.S. PATENT DOCUMENTS

| | | | |
|---|---|---|---|
| 5,069,769 A | 12/1991 | Fujimiya et al. | 204/182.8 |
| 5,203,992 A | 4/1993 | Drouen | 210/198 |
| 5,447,612 A * | 9/1995 | Bier et al. | 204/450 |
| 5,627,643 A | 5/1997 | Birnbaum et al. | 356/344 |
| 5,858,195 A * | 1/1999 | Ramsey | 204/601 |
| 5,942,443 A | 8/1999 | Parce et al. | 436/514 |
| 5,955,028 A * | 9/1999 | Chow | 422/63 |
| 5,965,410 A * | 10/1999 | Chow et al. | 204/450 |
| 6,001,231 A * | 12/1999 | Kopf-Sill | 204/451 |
| 6,132,685 A * | 10/2000 | Kercso et al. | 422/63 |
| 6,136,171 A * | 10/2000 | Frazier et al. | 204/450 |
| 6,149,787 A * | 11/2000 | Chow et al. | 204/451 |
| 6,046,056 A1 | 4/2001 | Parce et al. | 436/514 |

FOREIGN PATENT DOCUMENTS

| | | |
|---|---|---|
| EP | 0 581 412 | 3/1993 |
| WO | WO98/00231 | 1/1998 |
| WO | WO99/12016 | 3/1999 |

* cited by examiner

Primary Examiner—Hal Wachsman
(74) Attorney, Agent, or Firm—Ritter, Lang & Kaplan LLP

(57) ABSTRACT

Techniques for analyzing an array of compounds utilizing a high throughput microfluidic system are provided. The system can translate a plurality of multiwell plates through various stations for analysis. Effects to sample compounds can be identified according to deviations in a steady state signal. Also, a user can enter the dwell times for sample compounds and a buffer solution so that the system will alternatingly inject the sample compounds and buffer solution into a microfluidic device according to the specified dwell times.

41 Claims, 22 Drawing Sheets

| OPERATOR | DESCRIPTION | LITERAL/LITERAL |
|---|---|---|
| + | ADDITION | 2+2 |
| − | SUBTRACTION | 4−2 |
| ^ | EXPONENTIATION | 2^2 |
| * | MULTIPLICATION | 2*2 |
| / | DIVISION | 2/2 |
| & | LOGICAL AND | 2&2 |
| \| | LOGICAL OR | 2\|2 |

| Function | Description |
|---|---|
| ABS(B) | The absolute value of the cell is returned. |
| ADD(A,B) | Adds the two elements. |
| IF(A,B,C) | If A is nonzero then B is returned. If A is zero then C is returned. A can contain one of the relational operators: greater than (>), less than (<), equal to (=), or not equal to (!) |
| ISEMPTY(B) | If B is empty then a 1 is returned. If B is not empty then a zero is returned. |
| MAX(A,B,...) | Returns the maximum value of all arguments. Accepts a variable number of arguments, up to a maximum of 30 arguments. Each argument can be a cell range, a float value, or an integer value. |
| MIN(A,B,...) | Returns the minimum value of all arguments. Accepts a variable number of arguments, up to a maximum of 30 arguments. Each argument can be a cell range, a float value, or an integer value. |
| NEG(B) | Changes the sign of the value. For example, NEG (15) = 15. |
| NOT(B) | If B is zero then a 1 is returned. If B is not zero then a zero is returned. |
| ROUNDUP(B,D) | Rounds the value up to the next whole number, using the specified number of decimal places (D). A zero can be used for no decimal places. Negative precision specifies tenths, hundredths, etc. |
| ROUND(B,D) | Rounds the value up to the nearest whole number, using the specified number of decimal places (D). A zero can be used for no decimal places. Negative precision specifies tenths, hundredths, etc. |
| SUM(B,C,...) | Sums cells or blocks. Accepts a variable number of arguments, up to a maximum of 30 arguments. Each argument can be a cell range, a float value, or an integer value. |
| TRUNCATE(B,D) | Rounds the value down to the next whole number, using the specified number of decimal places (D). A zero can be used for no decimal places. Negative precision specifies tenths, hundredths, etc. |
| Sgfilter(W,X,Y,Z) | This is Savitsky Golay filter. Where the parameters are<br>W – SignalA as 1 or SignalB as 2<br>X – Filter width in number of data points<br>Y – Derivative order (e.g. 1 = slope, 2 = acceleration)<br>Z – Polynomial order |

*FIG. 17D*

SOFTWARE FOR HIGH THROUGHPUT MICROFLUIDIC SYSTEMS

BACKGROUND OF THE INVENTION

The present invention relates to the software and systems for high throughput micro fluidic analysis. More specifically, the invention relates to computer implemented processes for data analysis as well as graphical user interface techniques for directing and analyzing data from high throughput microfluidic systems.

Considerable work is now underway to develop microfluidic systems, particularly for performing chemical, clinical and environment analysis of chemical and biological specimens. The term "microfluidic" refers to a system or device having one or a network of chambers and/or channels, which have micro scale dimensions, e.g., having at least one cross sectional dimension in the range from about 0.1 $\mu$m to about 500 $\mu$m. Microfluidic substrates are often fabricated using photolithography, wet chemical etching, injection molding, embossing, and other techniques similar to those employed in the semiconductor industry. The resulting devices can be used to perform a variety of sophisticated chemical and biological analytical techniques.

Micro fluidic analytical systems have a number of advantages over conventional chemical or physical laboratory techniques. For example, microfluidic systems are particularly well adapted for analyzing small sample sizes, typically making use of samples on the order of nanoliters and even picoliters. The channel defining substrates may be produced at relatively low cost, and the channels can be arranged to perform numerous analytical operations, including mixing, dispensing, valving, reactions, detections, electrophoresis, and the like. The analytical capabilities of microfluidic systems are generally enhanced by increasing the number and complexity of network channels, reaction chambers, and the like.

Substantial advances have recently been made in the general areas of flow control and physical interactions between the samples and the supporting analytical structures. Flow control management may make use of a variety of mechanisms, including the patterned application of voltage, current, or electrical power to the substrate (for example, to induce and/or control electrokinetic flow or electrophoretic separations). Alternatively, fluid flows may be induced mechanically through the application of differential pressure, acoustic energy, or the like. Selective heating, cooling, exposure to light or other radiation, or other inputs may be provided at selected locations distributed about the substrate to promote the desired chemical and/or biological interactions. Similarly, measurements of light or other emissions, electrical/electrochemical signals, and pH may be taken from the substrate to provide analytical results. As work has progressed in each of these areas, the channel size has gradually decreased while the channel network has increased in complexity, significantly enhancing the overall capabilities of microfluidic systems.

One particularly advantageous application for microfluidic techniques is to screen collections of large numbers of samples. There has long been a need to rapidly assay numerous compounds for their affects on various biological processes. For example, enzymologists have long sought improved substrates, inhibitors, and/or catalysts for enzymatic reactions. The pharmaceutical industry has focused on identifying compounds that may block, reduce, or enhance the interactions between biological molecules, such as the interaction between a receptor and its ligand. The ability to rapidly process numerous samples for detection of biological molecules relevant to diagnostic or forensic analysis could also have substantial benefits for diagnostic medicine, archaeology, anthropology, and modem criminal investigations. Modem drug discovery has long suffered under the limited throughput of known assay systems for screening collections of chemically synthesized molecules and/or natural products. Unfortunately, the dramatic increase in the number of test compounds provided by modem combinatorial chemistry and human genome research has overwhelmed the ability of existing techniques for assaying sample compounds.

High throughput screening assay systems and methods have been previously described in for example, published PCT Patent Application No. WO 98/00231, U.S. Pat. No. 5,779,868 and U.S. Pat. No. 5,942,443, which are all hereby incorporated by reference for all purposes. These patents and applications describe, among other things, a microlaboratory system that can sequentially introduce a large number of test compounds (typically contained in a multiwell plate) into a large number of assay chips or microfluidic devices. This advantageous system allows testing of a large number of sample compounds with a compact sample handling arrangement, while the manipulation of picoliter or nanoliter volumes of chemicals can both enhance the speed of each chemical analysis and minimize and sample and waste product volumes. Hence, such a microlaboratory system represents a significant advancement for handling and testing large numbers of chemical and biological compounds.

Nevertheless, it would be beneficial to have innovative techniques for identifying sample compounds that demonstrate an effect during assay processing and preferably, ways of verifying the accuracy of the measured effect and/or identified sample compound. Additionally, it would be beneficial to have innovative software and systems that would allow the researcher to more easily direct the operation of the high throughput microfluidic system and greater flexibility in analyzing the data acquired by the high throughput microfluidic system.

SUMMARY OF THE INVENTION

The present invention provides innovative software and systems for analyzing data from and directing the operation of high throughput microfluidic systems. In one aspect of data analysis, a signal is analyzed to identify sample compounds that demonstrate an observed effect on a reaction. The effect can also be verified by further analysis. In one aspect of system direction, users can configure the high throughput microfluidic systems by entering information utilizing a graphical user interface. For example, the user can specify the sample plate that is being utilized, set dwell times for sample compounds and buffer solutions, specify characteristics for dye fluids, specify characteristics for guard fluids, set sample dilution parameters, and the like. Additionally, the user can view a graph of measured signal strength as sample compounds flow past the detection point of a microfluidic device while viewing information relating to a script that directs the flow of the system and observing values for channels specified by the script. Some embodiments are described below.

In one embodiment, the invention provides a computer implemented method of analyzing an array of sample compounds utilizing a microfluidic device. A signal corresponding to sample compounds being driven through the microfluidic device are received. The signal is analyzed to detect a deviation. The sample compound that caused the deviation is then identified. The deviation can be the result of, for example, an inhibitor or an enhancer of an enzymatic reaction.

In another embodiment, the invention provides a computer implemented method of analyzing an array of sample compounds utilizing a microfluidic device. User input specifying a dwell time for the sample compounds is received. Also, user input specifying a dwell time for a buffer solution is received. The sample compounds and buffer solution are then alternatingly injected into the microfluidic device for the specified dwell times for the sample compounds and buffer solution. In preferred embodiments, the microfluidic device includes at least two intersecting channels with a cross sectional dimension in a range of about 0.1 $\mu$m to about 500 $\mu$m.

In another embodiment, the invention provides a computer implemented method of analyzing an array of sample compounds utilizing a microfluidic device. A graph of a measured signal strength as the sample compounds flow past a detection point of the microfluidic device is displayed. Information relating to a script that directs the flow of the sample compounds past the detection point is also displayed. A value for a channel specified by the script is displayed and in preferred embodiments, a user can enter a formula that will be calculated so that the result can be displayed.

A further understanding of the nature and advantages of the invention described herein may be realized by reference to the remaining portions of the specification and attached drawings.

BRIEF DESCRIPTION OF THE DRAWINGS

FIGS. 17A–17E show examples of windows and information that can be entered into the windows in order to analyze data from the high throughput microfluidic system.

DETAILED DESCRIPTION OF EMBODIMENTS

The present invention provides software and systems for analyzing data from and directing high throughput microfluidic systems, which are designed to introduce large numbers of sample compounds into a channel network of a microfluidic device. The high throughput microfluidic systems typically facilitate sequential introduction of a large number of sample compounds into the channel network from a plurality of multiwell plates (or other array structures). The systems will find applications in screening large numbers of different compounds for their effects in a wide variety of chemical, and particularly biochemical systems. More specifically, the systems will have applications for general assay screening in diagnostic and other clinical settings, for pharmacological agent screening, and the like. However, the invention is not limited to any specific system, implementation or application. Therefore, the description that follows is for illustration purposes and not for limitation.

Figure 1:
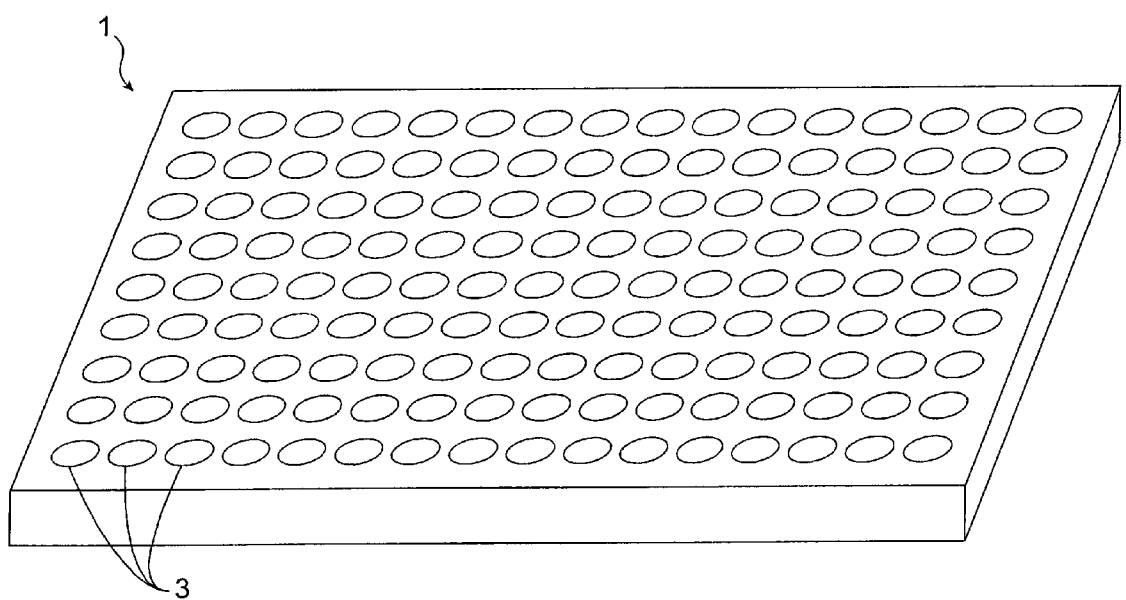
FIG. 1 shows an embodiment of a plate including sample wells.

FIG. 1 shows a plate including multiple wells for holding and transporting an array of sample compounds. A plate 1 includes multiple wells 3 that are designed to retain fluids. Although microfluidic devices typically operate on very minute volumes of fluid, the wells are preferably designed large enough to allow for dilution in wells 3 of plate 1. Plates for use with the invention can be formed of a variety of materials and in a variety of ways. For example, the plates can comprise Teflon, polyethylene, polypropylene, polystyrene, polyvinylchloride, glass, ceramic, metal or the like. In some embodiments, a metallic multiwell plate can assist in injecting the samples by applying a potential to the plate material, the whole plate acting as an electrode. Such metallic plates will preferably comprise titanium, stainless steel, or the like.

In other embodiments, a multiwell plate can have a conductive layer disposed over a non-conductive substrate. The wells could be formed in a plate of glass, ceramic, a polymer, or the like, over which a layer of metal is sputtered, plated, or otherwise deposited so as to operatively couple an electrical power source to samples disposed in the wells. A wide variety of metal layers might be used, including aluminum, titanium or the like, with deposition techniques such as those developed for use in the fabrication of integrated circuits and recording media. In some embodiments, a simple metallic foil might be applied over a multiwell plate.

Plate 1 is shown including 96 (8×12) separate wells. In other embodiments, the plates include 384 wells (or more). The number of wells in a plate can be varied according to the specific application and performance desired. In preferred embodiments, the plates are designed in such a manner that allow them to be reused. In other embodiments, the "wells"

are dried or solid sample compounds on a substrate onto which a liquid is dispensed before being drawn in the microfluidic system. Accordingly, the term well can include any technique for storing sample compounds at specific locations.

Figure 2:
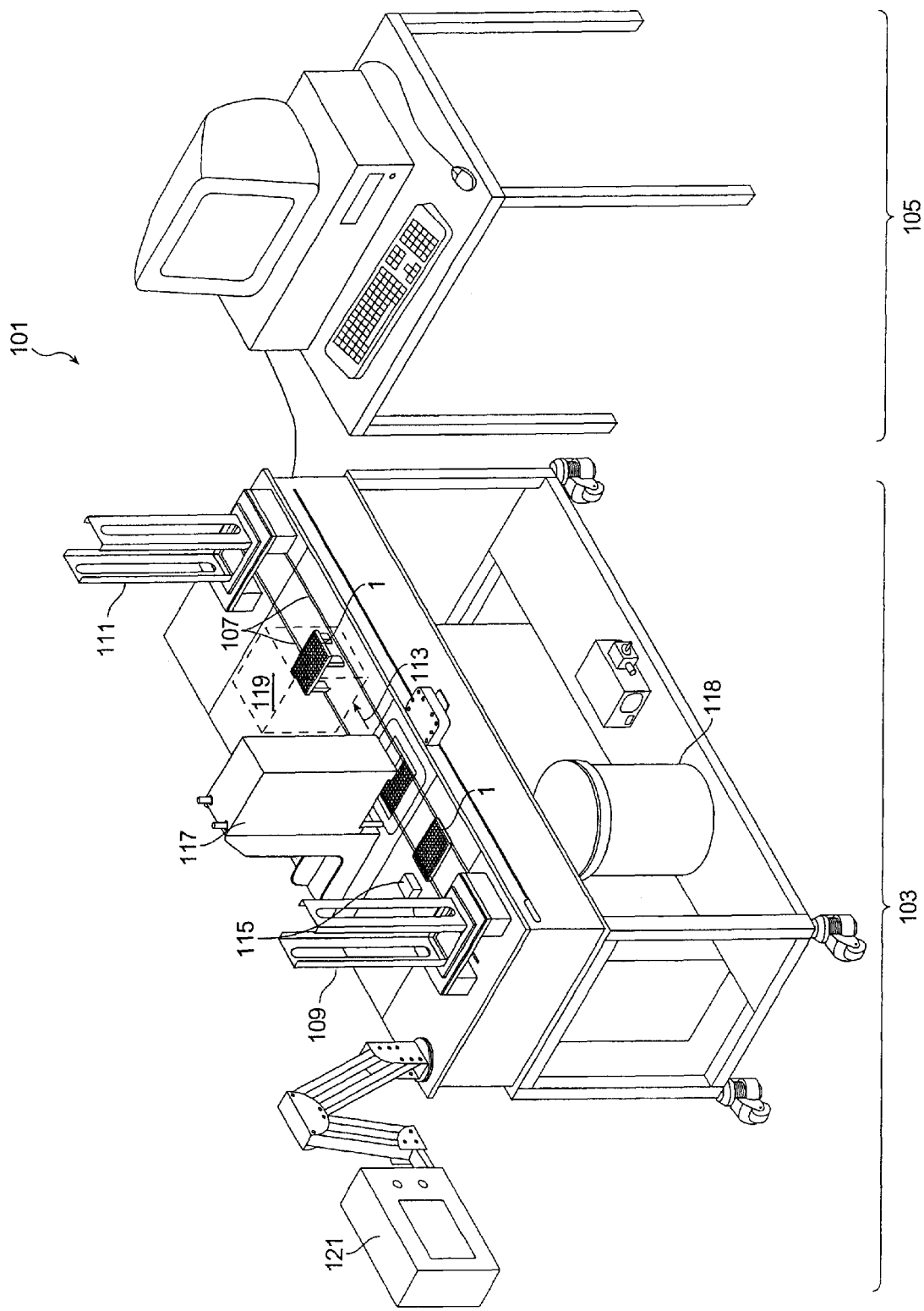
FIG. 2 shows a high throughput microfluidic system including a screening station and a computer system.

Plates that retain sample compounds, and potentially other materials, can be analyzed by the high throughput microfluidic system shown in FIG. 2. High throughput microfluidic system 101 includes a high throughput screening station 103 and a computer system 105, which are shown in electrical communication such as using a serial line. System 103 generally analyzes sample compounds by translating multiwell plates along a conveyer system 107 from an input stack 109 to an output stack 111 along a plate path 113. As the plates travel sequentially along path 113 they pass through a bar code reader station 115, a dilution station 117, and a test station 119 (shown schematically here as a clear box and described in more detail in reference to FIG. 3). At test station 119, the plates are moved from path 113 by lifters, and the samples contained in the wells of the plate are sequentially introduced into the channel network of a microfluidic device.

The description herein below will generally refer to a test conducted on sample liquids. In many instances, the number and/or nature of the liquids to be sampled may generate sample handling problems. For example, in chemical screening or drug discovery applications, libraries of compounds for screening may number in the thousands and hundred thousands. As a result, such libraries require extremely large numbers of sample plates, creating difficulties in sample storage, manipulation, and identification. Additionally, in some cases, specific sample compounds may degrade, complex, or otherwise possess relatively short active half-lives when stored in liquid form. This could potentially result in suspect results where samples are stored in liquid form for long periods prior to screening.

Sample compounds may be contained in the wells of multiwell plate 1. Multiwell plates typically comprise an array of blind holes or wells, and are commercially available in a variety of forms particularly advantageous multiwell plates include a 96 well clear polymer plate sold by Corning, with an orthogonal 8×12 array of wells. An alternative 384 well plate is commercially available from Genetix, in which the wells are arranged in a 16×24 array. These plates are very roughly 3.5 inches in width, 5 inches in length, and 3/8 inch in height. The present invention will also find applications with a wide variety of alternative plate and sample array structures.

Conveyor system 107 preferably comprises a pair of flexible drive belts driven by a shaft of a single motor. In the embodiment shown, the position of plates 1 along path 113 is controlled using pins extending upward between the belts. These pins can block progress of plates 1 at dilution station 117, testing station 119, or the like, so that the belts of the conveyor system can run continuously. Alternatively, conveyor system 107 might make use of stepper motors, and arm moveable in linear or polar coordinates, or a wide variety of alternative transportation mechanisms. As shown using flexible drive belts, the return path for each belt is disposed below an upper surface or deck of high throughput screening station 103, the belts comprising the elastomeric polymer tubes. Conveyor system 107, input stack 109, output stack 111, the conveyor stop pins, and many of the other plate handling components of high throughput screening station 103 are commercially available through Carl Creative Systems of Harbor City, Calif.

Input stack 109 comprises a commercially available downstacker for lowering plates 1 onto conveyor system 107. Similarly, output stack 111 comprises a commercially available upstacker for removing plates 1 from the conveyor system. These commercially available plate handling modules controllably raise and lower the plates contained therein per instructions signals from a processor as will be described herein below.

Bar code reader station 115 includes an optical bar code reader oriented towards a back edge of plate 1. The bar codes disposed on the back edge of plate 1 may provide information regarding the specific samples contained the wells of the plates, or may alternatively comprise a plate identifier so that the sample and/or test parameters are retrieved from a look-up table by the processor. A sample's data might include any or all of the identity of the sample compounds, the quantity, purity, source, or other sample specific information, or may provide test specific information regarding dilution ratios, reaction times, the number or format of samples in the array, or the like. A wide variety of alternative sample management stations may be provided instead of or in addition to bar code reader 115, before and/or after each reaction or test station.

Dilution station 117 comprises a multichannel dispense apparatus for controllably distributing liquids into the wells of plates 1. Where plates 1 include 96 wells, dilution station 117 will typically have a 96 channel dispense head. Similarly, where 384 well plates are used, a 384 channel dispense head may be provided. Alternatively, a 96 channel dispense head can distribute liquid into 384 wells (or more) by moving the dispense head relative to the plate (or vice versa). Further details of an embodiment of a dilution station can be found in U.S. Pat. No. 6,132,685, which has been previously incorporated by reference.

Dilution station 117 will typically be used to reconstitute the samples in aqueous assay buffers. As microfluidic analysis can make use of very small volumes of sample compounds, the sample may (at least initially) have a starting volume of less than one microliter. Dilution station 117 may variably dilute such volumes with dilution ratios of up to over 1,000 using the small wells of multiwell plates. Dilution station 117 will typically make use of multi channel pipettor heads, but may alternatively use techniques such as piezoelectric dispensing or pin transfer of small droplets to controllably transfer sub-microliter volumes of liquid. Dilution station 117 can draw dilution fluids through tubes from a container 118.

The inclusion of one or more reaction stations (such as dilution station 117) along a common path 113 with test station 119 provides great flexibility in carrying out screening experiments. For example, the proximity of dilution station 117 with the microfluidic device at the test station allows the user to precisely control and minimize the time delay between reconstitution of test compounds in aqueous buffer and their analysis for binding or inhibitory activity. By flexibly controlling the separation time between dilution and testing, time dependent characteristics of the test compounds (particularly those that are unstable in aqueous environments) can be characterized.

The use of a bi-directional conveyor belt, which might allow a plate 1 to be transferred back and forth repeatedly between a reaction station and a test station, further enhances the flexibility of sample testing. As an example, high throughput screening system 103 having a single dilution station 117 and a single test station 119 with a bi-directional conveyor belt capable of translating plates back and forth could be used to define a wide variety of different reconstitution and dilution sequences. Starting with a volume of 0.3 microliters of compound in DMSO in each well of multiwell plate 1, one could reconstitute samples into a total volume of 30 microliters (a 100-fold dilution of the compounds, 1% DMSO). These reconstituted samples could then be subjected to a microfluidic assay by moving plate 1 from dilution station 117 to test station 119, after which the plate could be returned to the dilution station for dilution of the tested samples to 300 microliters of total volume (a 1,000-fold dilution of each compound, 0.1% DMSO). The plate could again move to test station 119 for re-assaying at this new concentration. This process can be repeated and/or varied as desired to enhance the predicted nature of the data for relative potency.

A display interface 121 can include a display screen and processor in order to allow a user to direct the operation of high throughput screening system 103. The display interface can be utilized to control some or all aspects of the high throughput screening station including conveyor system 107, dilution station 117, and test station 119. Alternatively or in addition to, computer system 105 can be utilized to direct the operation of high throughput screening station 103 and to analyze data that is obtained from the high throughput screening station. In some embodiments, computer system 105 can be integrated with high throughput screening station 103. Computer system 105 will be discussed in reference to FIGS. 6 and 7.

Figure 3:
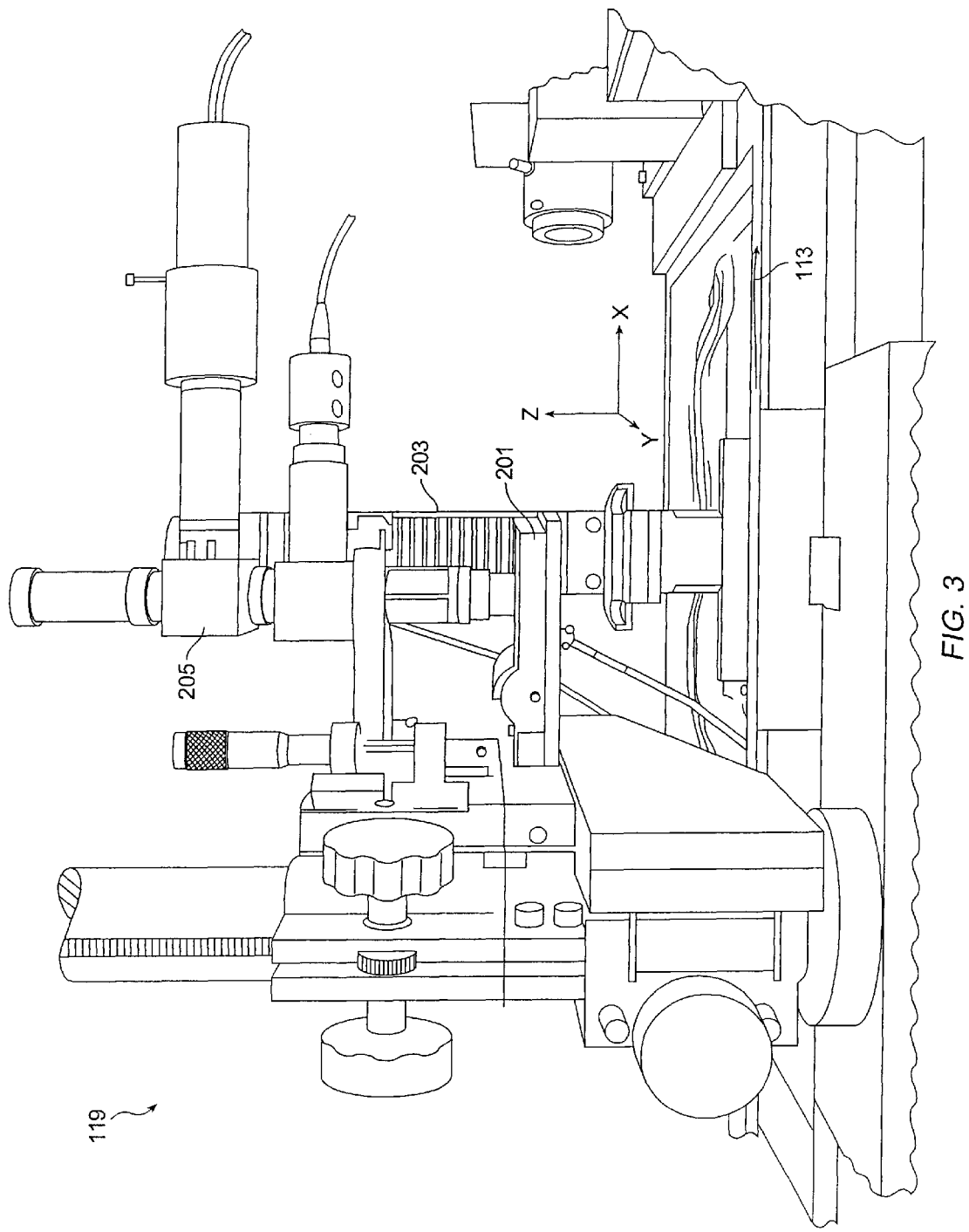
FIG. 3 shows a test station for the screening station of FIG. 2.

The structure and arrangement of the components at test station 119 can be understood with reference to FIG. 3. Test station 119 generally includes a microfluidic device disposed within a clamshell interface structure 201. X-Y-Z robot arm 203 lifts a multiwell plate from adjacent plate path 113 and sequentially aligns the wells of the plate with a pipettor extending downward from the microfluidic device through a base of clamshell interface 201 (see FIG. 4). Optical detection system 205 optically monitors the assays taking place within the channel network of the microfluidic device. In alternative embodiments, samples may be introduced from above the microfluidic device, detection system 205 may be disposed below the clamshell base and the like. As can be understood with reference to FIG. 3, the optical detection system and clamshell interface are supported from a front edge of the high throughput screening station (to one side of path 113), while robotic arm 203 is supported by a back edge of the high throughput screening station. Stop pins are used to accurately position the plates along path 113 at the test station, allowing the belts of conveyor system 107 to run continuously.

The ability of robotic arm 203 to move plates 1 in three dimensions allows the arm to perform at least three different functions. First, the arm lifts plates in the vertical or Z direction arm to generally transport the plates from adjacent plate path 113 to an adjacent microfluidic device. This allows the microfluidic device to remain at a fixed location, rather than subjecting the various optical and electrical components that interface with the microfluidic network to repeated movement. Secondly, the robotic arm positions the plate accurately in the X-Y plane to sequentially align the wells of the plate with a pipettor, thereby allowing the samples in the wells to be sequentially introduced into the channel network of the microfluidic device. Thirdly, once the wells are aligned with the pipettor, the robotic arm can lift the plate to bring the sample in the aligned well into contact with the pipettor, thereby allowing the robotic arm to act as a member of the fluid introduction system. An exemplary X-Y-Z robotic positioning system is commercially available from Parker-Hannifin Corporation of Harrison City, Pa. This exemplary arm structure is built up from three independent linear actuators.

The structure of pipettor 46 and a method for introducing the samples into the channel network is described in co-pending U.S. Pat. No. 5,958,203, previously incorporated herein by reference. Alternatively, a wide variety of fluid introduction techniques might be used.

Figure 4:
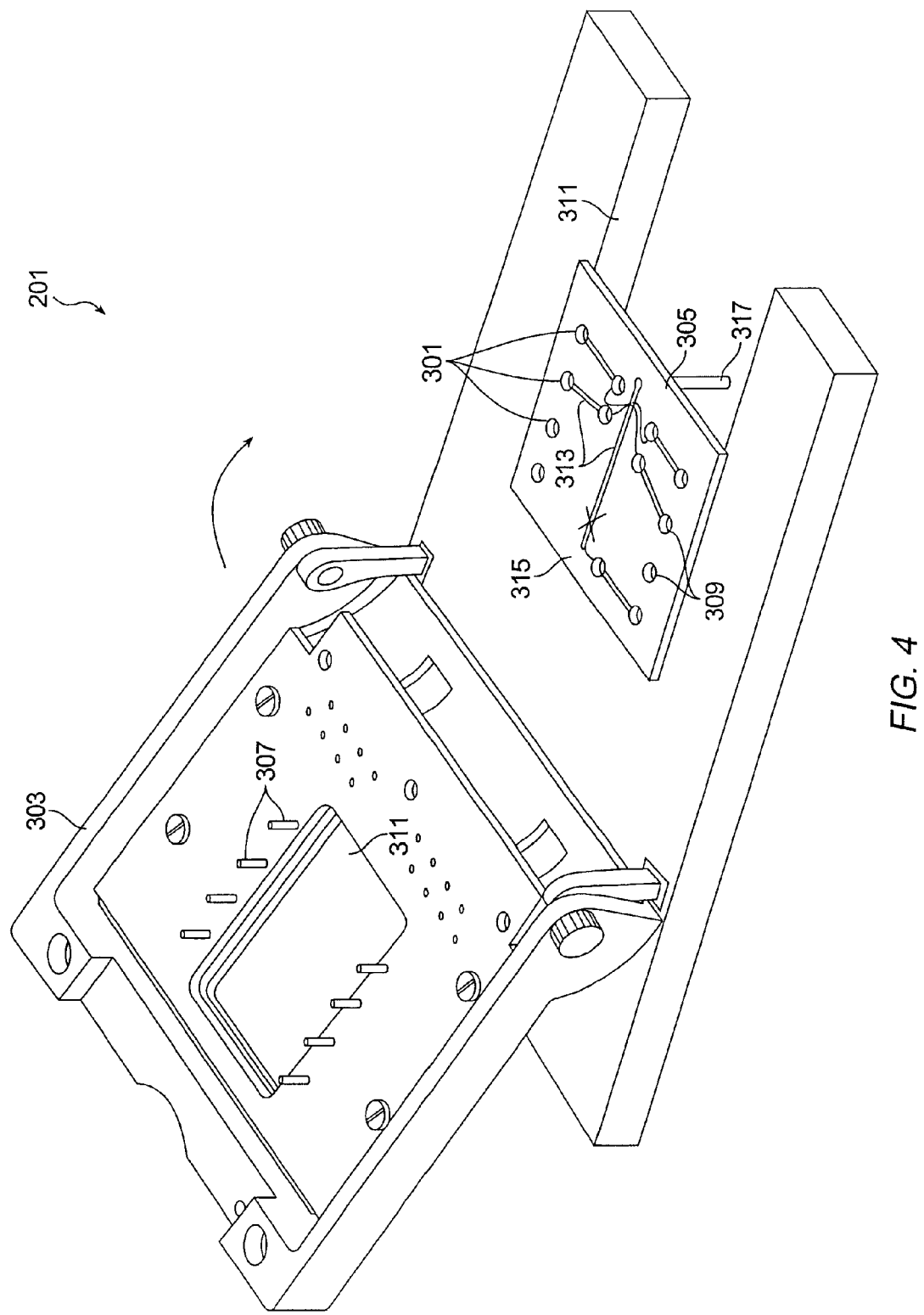
FIG. 4 shows a microfluidic device resting on a base of a clamshell support structure, showing a lid of the clamshell support structure in an open position.

Referring now to FIG. 4, clamshell interface 201 generally includes a base 301 and a lid 303 pivotally coupled to the base. The base and lid restrain a microfluidic device 305 therebetween, and electrodes 307 mounted on the lid extend into chip wells or ports 309 of the microfluidic device when lid 303 is in a closed position. One or more windows 311 open through base 301 or lid 303 to provide optical access for monitoring the assays in microfluidic device 305. Related structures are described in U.S. Pat. No. 5,989,402, the full disclosure of which is hereby incorporated by reference.

As shown, microfluidic device 305 is generally fabricated with a planar substrate. Suitable substrate materials are generally selected based on their compatibility with the conditions present in the particular operation to be performed by the device. Such conditions include extremes of pH, temperature, ionic concentration, and application of electrical fields. Additionally, substrate materials are also selected for their inertness to critical components of an analysis or synthesis to be carried out by the system.

Useful substrate materials include glass, quartz, and silicon, as well as polymeric substrates, e.g., plastics. In the case of polymeric substrates, the substrate materials may be rigid, semi-rigid, or non-rigid, opaque, semi-opaque, or transparent, depending on the use for which they are intended. For example, devices which include an optical or visual detection element will generally be fabricated, at least in-part, from transparent materials so as to allow (or at least facilitate) that detection. Alternatively, transparent windows of, e.g., glass or quartz, may be incorporated into the device for these types of detection elements. Additionally, the polymeric materials may have linear or branched backbones, and me crosslinked or non-crosslinked. Examples of particularly preferred polymeric materials include, e.g., polymethylmethacrylete (PMMA), polydiemthylsiloxanes (PDMS), polyurethane, polyvinylchloride (PVC), polystyrene, polysulfone, polycarbonate, and the like.

Typically, the substrate will comprise an upper portion through which ports 301 are drilled (or otherwise fabricated), and a lower portion having microfluidic channels 313. The upper portion is bonded to the lower portion so that the channels and ports are in fluid communication. Channels may also be formed in the upper portion as well as, or instead of, the lower portion. In addition to allowing access to the fluid within the channels for electric coupling *using electrode 307 or the like) chip wells or ports 309 may act as reservoirs for fluids to be used in the assaying of the samples. The structure of the substrate and the use of electrokinetics as a transportation mechanism within microfluidic channels more fully described in Published PCT Application Nos. WO 98/00707 and WO 96/04547, the full disclosures of which are incorporated herein by reference. In particularly preferred aspects, pressure differentials are used in conjunction with optimized channel configurations to move materials through the channels of the device. Such systems are described in, for example, U.S. patent application Ser. No. 09/233,700, filed Jan. 19, 1999 (now issued as U.S. Pat. No. 6,150,119), 09/277,367, filed Mar. 26, 1999 (pending), and 09/238,467, filed Jan. 28, 1999 (pending), which are all hereby incorporated by reference.

A typical chip for assaying biochemical compounds might include ports containing paired buffer solutions, and enzyme port, a waste port, and the like, while the optical detection system may be directed to a detection point 315 along the channel, along a microfluidic reaction chamber, or the like. An exemplary substrate might include channels of varying depths, such as main channels having a depth of 15 µm, with smaller side channels having a depth of 1.5 µm. These channels will typically have widths of in the range from about 50 µm to about 80 µm, and may be defined using many of the techniques developed for processing of semiconductors, including photolithography, etching, and the like.

As can be seen in FIG. 4, microfluidic device 40 includes at least on pipettor 317 extending below the microfluidic substrate. Pipettor 317 comprises a tubular structure affixed to the substrate of the microfluidic device, and may extend at an angle to the plane of the substrate. In such embodiments, clamshell interface device 201 may support microfluidic device 305 so that the plane of the substrate is at an angle from a horizontal reference plane, the substrate optionally being at a vertical orientation so that the side mounted pipettor is vertical to more easily enter the vertical wells of dense multiwell plates. In other embodiments, a wide variety of techniques might be used to introduce samples, including differential pressures, conventional micropipettors, piezoelectric dispenser, pin transfer systems, reservoir/input ports extending through the upper and lower substrate portions, or the like.

While microfluidic device 305 is here illustrated as having a single pipettor, it should be understood that many embodiments of the present invention will include a plurality of pipettors for simultaneously injecting and processing samples in parallel assay channels, thereby providing a higher throughput for the system. One preferred chip configuration might have a linear array of 12 sample probes with nine millimeter or 4.5 millimeter spacing therebetween, for compatibility with both 96 well and/or 384 well microtiter plates. Such muliplex chip configurations might have each sample pipettors or probes leading to several parallel assay channels, so that multiple assays are run in the same chip. In general, it would be desirable to have common reagents reservoirs feeding all parallel assay channels to simplify loading of the chip.

Design considerations for multiplexed chips will include microfluidic criteria (e.g., flow rates and mixing times, resistance to hydrodynamic flow, filling issues), electrical criteria (e.g., the total resistance of each fluidics pathways, the applied voltages or currents required to generate appropriate electrical fields), fabrication criteria (e.g., yields for making connections between pipettor and microfluidic device 305 might place practical limitations on the multiplexing of a single chip), and assay criteria (e.g., reaction kinetics, protein adsorption issues, etc.).

Although the exemplary embodiment is generally described herein for use with plates having 96 or 384 wells, it should be understood that the present invention is adaptable for use with multiwell plates having higher density compound storage formats, including those with 1,536 wells. While the chip need not be multiplexed to densities equivalent to those of the plates, a multiplexed chip having an array of sample input ports (the ports typically aligned as a linear array) with the proper spacing between ports and the proper port size and structure (for example, using a coaxial pipettor/electrode arrangement) can increase throughout and be compatible with one or more high density plate configurations. For example, a linear array of 12 pipettors might be able to input samples from 96, 384, and 1,536 well plates.

To facilitate fabrication of high density multiplex chip structure, pipettor 317 will optionally incorporate a sample electrode, rather than relying on separate pipettors and sample electrode structures to electrokinetically inject the sample into the sample input port. For example, a layer of platinum may be sputter coated onto the pipettor structure, so that the platinum provides an electrode that is coaxial with the inflow port. Alternatively some or all of plate 1 might be formed of an electrical conductor. For example, plate 1 might comprise a metal (preferably being titanium, stainless steel, aluminum, or the like) so that the entire plate may be used as an electrode.

The collection efficiency of the optics might be improved by reducing the thickness of the cover portion of the substrate, the cover portion typically comprising a sheet of glass or other transparent material boded over the remaining substrate to define the upper surfaces of the channel network. As this cover often includes the openings which define ports 309, an additional well plate extending over the ports may be included to allow the ports to retain sufficient volume to act as reagent reservoirs for sustaining long screening experiments. This additional reservoir plate extending over port 309 might be formed of plastic or the like, and/or might include molded fluid connectors to provide a convenient mechanism for coupling the microfluidic channel network with an external reagent reservoir. One or more of the materials used in fabricating microfluidic device 305 may include surface coatings to reduce protein adsorption, selectively control electroosmatic flow and the like. Other improvements in microfluidic chip technology will be incorporated with these new multiplexed devices, including the use of on chip salt new multiplexed devices, including the use of on chip salt bridges for isolating biological reagents from potential electrochemical degradation near the control electrodes.

Figure 5:
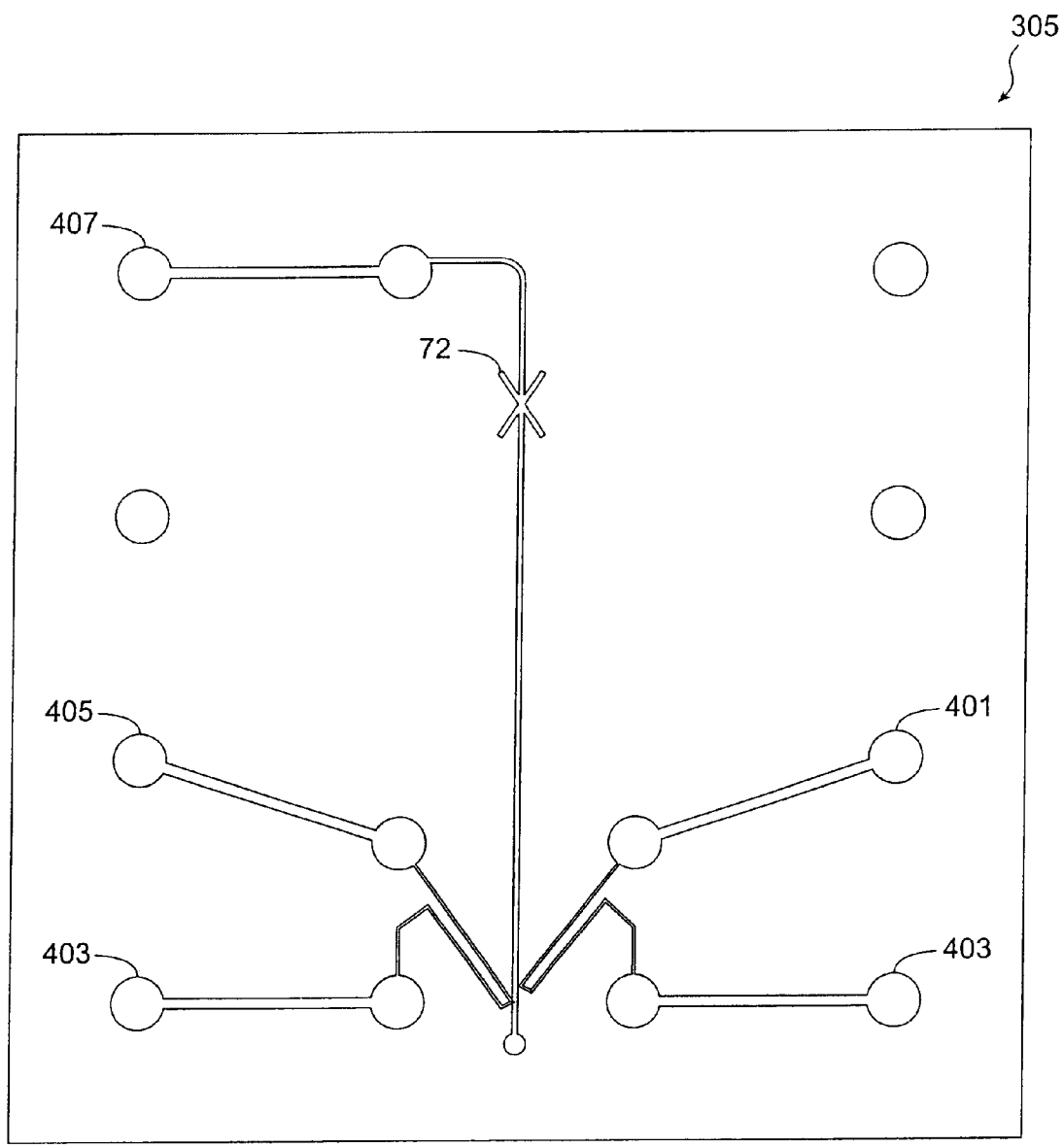
FIG. 5 illustrates an exemplary microfluidic device, showing the channel system and wells of ports.

FIG. 5 shows an embodiment of a microfluidic device for use with the invention. Microfluidic device 305 includes a substrate well 401, paired buffer wells 403 and an enzyme well 405. As fluids including the sampled compounds are driven through the main channel, optical measurements are taken at detection point 72. The fluids are then collected at a waste well 407. In preferred embodiments, the acceleration and speed of fluids in the microfluidic device are varied in order to keep well-to-well times for all wells on a plate.

Figure 6:
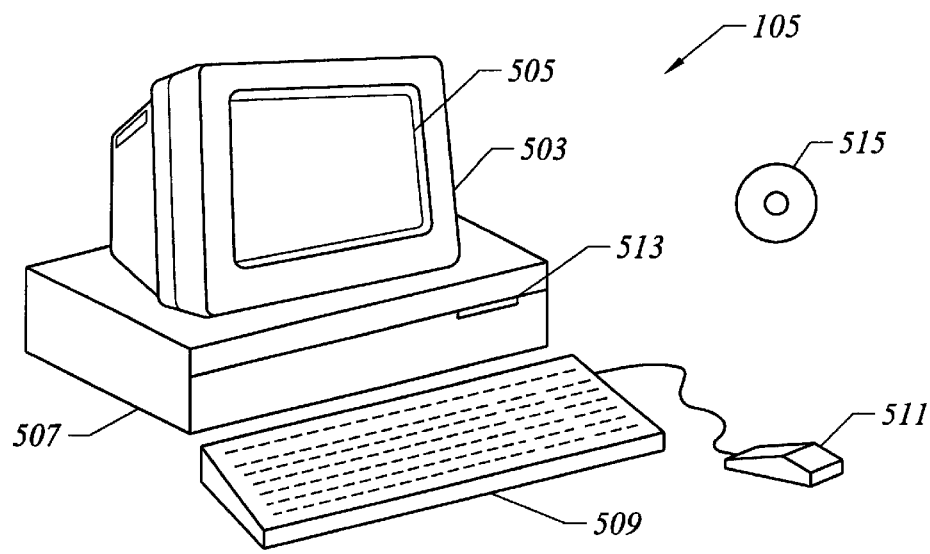
FIG. 6 illustrates an example of a computer system that may be utilized to execute the software of an embodiment of the invention.

FIG. 6 illustrates an example of a computer system that can be used to execute the software of an embodiment of the invention. FIG. 6 shows a computer system 105 that includes a display 503, screen 505, cabinet 507, keyboard 509, and mouse 511. Mouse 511 can have one or more buttons for interacting with a graphical user interface. Cabinet 507 houses a CD-ROM drive 513, system memory and a hard drive (see FIG. 7) which can be utilized to store and retrieve software programs incorporating computer code that implements the invention, data for use with the invention, and the like. Although CD-ROM 515 is shown as an exemplary computer readable storage medium, other computer readable storage media including floppy disk, tape, flash memory, system memory, and hard drive can be utilized. Additionally, a data signal embodied in a carrier wave (e.g., in a network including the Internet) can be the computer readable storage medium.

Figure 7:
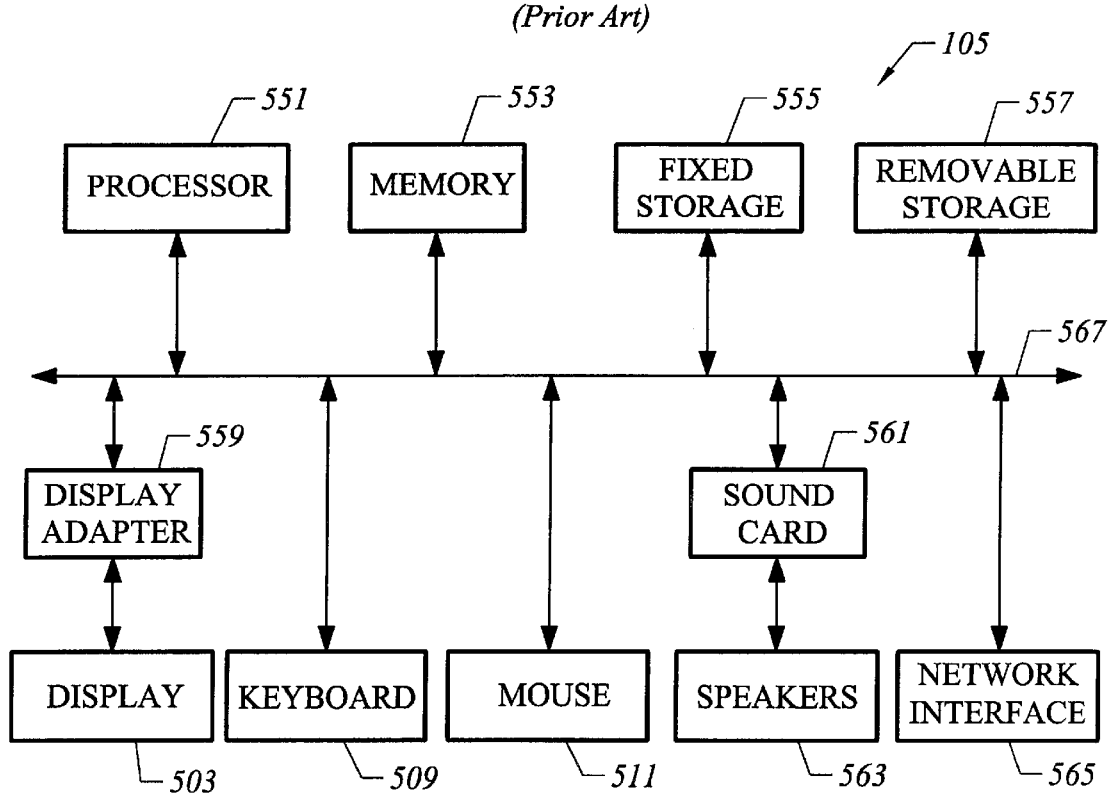
FIG. 7 illustrates a system block diagram of the computer system of FIG. 6.

FIG. 7 shows a system block diagram of computer system 105 used to execute the software of an embodiment of the invention. As in FIG. 105, computer system 105 includes monitor 503 and keyboard 509, and mouse 511. Computer system 105 further includes subsystems such as a central processor 551, system memory 553, fixed storage 555 (e.g., hard drive), removable storage 557 (e.g., CD-ROM drive), display adapter 559, sound card 561, speakers 563, and network interface 565. Other computer systems suitable for use with the invention can include additional or fewer subsystems. For example, another computer system could include more than one processor 551 (i.e., a multi-processor system) or a cache memory.

The system bus architecture of computer system 105 is represented by arrows 567. However, these arrows are illustrative of any interconnection scheme serving to link the subsystems. For example, a local bus could be utilized to connect the central processor to the system memory and display adapter. Computer system 105 shown in FIG. 7 is but an example of a computer system suitable for use with the invention. Other computer architectures having different configurations of subsystems can also be utilized.

Prior to initiating a typical screening run, e.g., for an enzyme inhibition assay, microfluidic device 305 will generally be primed with an appropriate running buffer and loaded into clamshell interface structure 201 of high throughput station 103. Any ports 309 that serve as reservoirs can be filled with biological reagents. The detection optics may then be aligned with the detection point on microfluidic device 305, preferably by initiating a flow of the enzyme and fluorogenic substrate. The detection equipment can then be manually adjusted so that the position and focus of the optics maximize the fluorescence signal.

The user will generally input parameters for controlling the system prior to performing the assays. For example, data file header information may be input or transferred to the host computer, together with any codes or inputs for controlling operational voltages and/or currents, injection dwell times, the number of samples per plate, the sampling pattern, or the like. The user will also input parameters for controlling the plate handling robotics. These robotic inputs may include the number of plates to be run, the type of plate being used, the volume of buffer to be dispensed into each well, number of aspiration/dispense cycles (to control mixing) or the like.

The plates will also be prepared by loading compounds to be tested into the wells prior to initiating the run. In many cases, the test samples will include, for example, inhibitors to be assayed for optimizing inhibition percentages.

Figure 8:
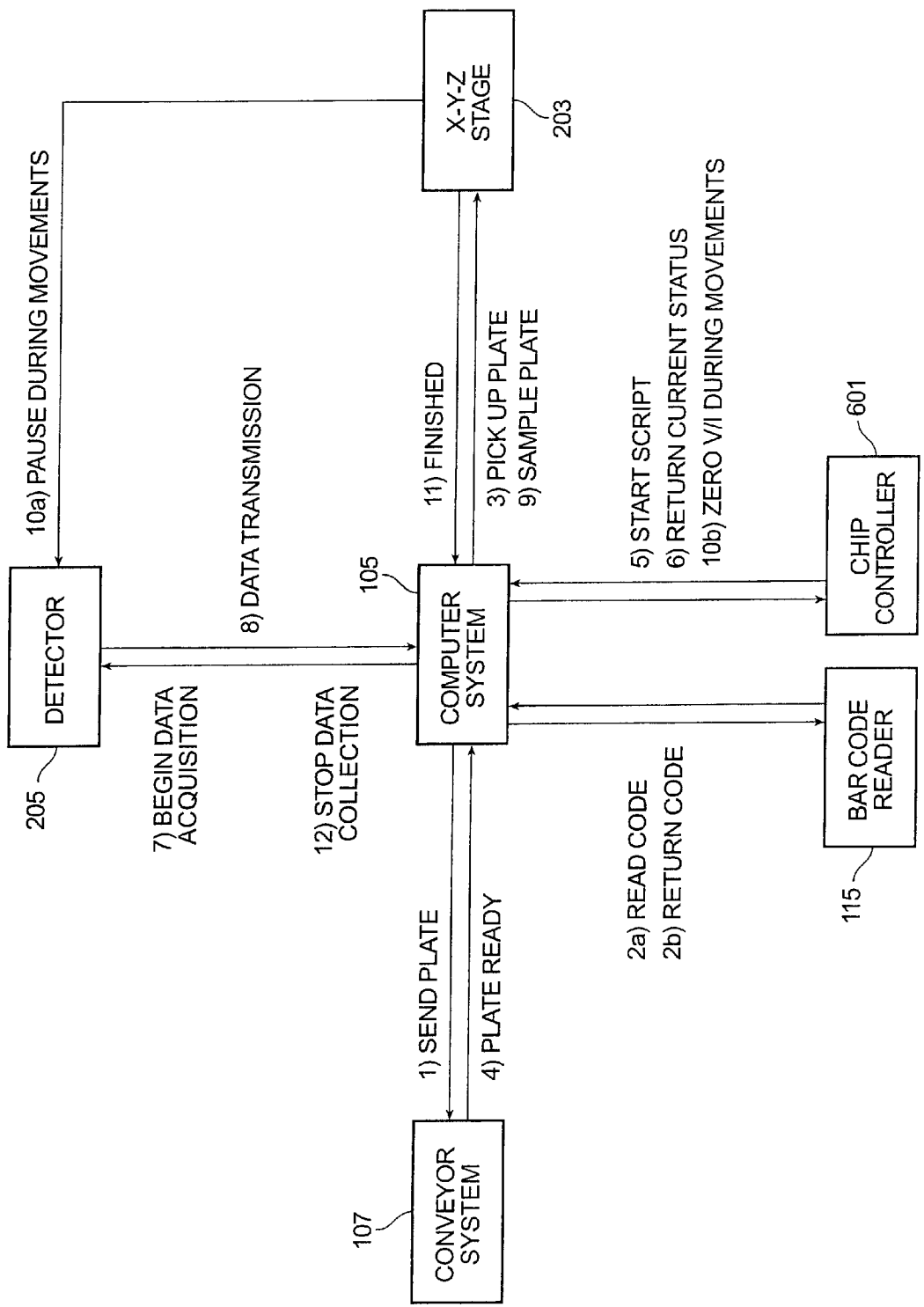
FIG. 8 is a schematic of the information and control system architecture and flow for the system of FIG. 2.

Once the data and plates have been loaded into high throughput station 103, the screening run can be initiated. Referring now to FIG. 8, computer system 105 will send a signal to the plate handling equipment to download a plate from input stack 109 to conveyor system 107. The computer system instructs bar code reader 115 to read the code as the plate passes by (or is held adjacent to) the bar code reader, and the bar code reader returns the read code to the computer system. This code will typically be logged into a data file for the run. In preparation for dilution, the dispense head will aspirate the appropriate volumes of assay buffer from buffer reservoir 118 located below the deck of system 103. Pins can be used to hold plate 1 in position at dilution station 117, and the dispense head then deposits the assay buffer in the wells so as to reconstitute the samples.

After the pins adjacent dilution station 117 lower to allow the plate to advance to test station 119, the plates are held in position at the test station using an additional pair of stop pins. Lifters lift plate 1 off conveyor 107, and the computer system sends a signal to robotic arm 203 to pick up the lifted plate. As the plate is lifted (and/or during testing of the samples) the dispense head can be lowered and rinsed in buffer below the deck of station 103, and the dispense head can also aspirate for the next dispense.

Once the system has the plate lifted and ready to be picked up by the robotic arm, the computer system can send a signal to a chip controller 601 on station 103 to start the chip operating script. The chip controller will return a signal to the computer system regarding the status of the chip operation. The computer system can further send a signal to the optical detection system to begin acquisition of data, with the resulting data signal returning to the computer system.

Robotic arm 203 lifts and sequentially positions the samples within the wells in fluid contact with the pipettor of microfluidic device 305. The microfluidic device draws in material only while the samples are in position, the chip controller and optical detection system both pausing between samples during movements of the robotic arm. The plate is repositioned beneath the chip to sequentially sample all of the desired compounds. Once all compounds have been sampled, the plate is returned to the conveyor belt and moves to upstacker 111. This cycle is repeated for the specified number of plates, typically with plates being simultaneously processed and/or moved by robotic arm 203, conveyor system 107, stacks 109, 111, dilution station 117, and test station 119.

While the test is underway, fluorescence data is stored, and this data can be subsequently processed to identify the regions of the data that contain information about the samples. Fluorescence intensities can be quantified for the regions of interest, and can be compared to positive controls so as to calculate the desired test results, for example, percent inhibition. Percent inhibition data could then be correlated with the particular well number (and the sample contained therein) on the multiwell plate.

The throughput of high throughput station 103 is determined by a number of factors. The total injection time for importing samples into the microfluidic network, including time for injection of running buffer, the high salt injection times, and the sample injection time may determine the dwell time of each sample at the fluid input port. These times should be adjusted to maximize throughput, while still maintaining well resolved sample plugs. The overhead or delay time associated with robotically positioning the multiwell plates during the injection cycle may also have a significant impact on throughput. The total robotic overhead time will typically be less than about 5 seconds per injection cycle, ideally being 3.5 seconds or less. Of this total, repositioning the plate to align the port with a sequential well will generally take less than a second. The delay associated with moving sequential plates between conveyor system 107 and the microfluidic device will have some effect on this total robotic overhead, although this delay can be minimized by using 384 well or higher density microtiter plates, as this operation need only be performed on a per plate basis (rather than per sample).

To enhance throughput, the control hardware and software, together with the chip interface structure, could be modified to accommodate multiplexed microfluidic devices, as described above. These modifications include adaptations to accommodate the physical dimensions of a larger, multiplexed chip, as well as the circuitry to control voltage and/or current electrically coupled with a greater number of fluidic channels. The control hardware and/or software could be modified to enable real time current and/or voltage sensing and feedback so as to control flow rate, the timing of injections into high salt plugs, and the like. Such a multiplexed microfluidic device controller might also require multiple analog to digital converters to handle multiple channel optical detection. Additional features which might be provided include selective thermostatic temperature control of the microfluidic device (throughout, for example, at least the range from about 25 to 37° C.), refrigeration of off-chip biological reagent reservoirs (for example, down to about 4° C. or less), and improved evaporation control for manually loaded chip reservoirs.

Additional software features which might be incorporated into the computer codes directing station 103 will preferably provide convenient, user defined protocols for synchronized switching of currents and voltages within microfluidic device 305. Synchronized positioning of the robotic arm, plate handling equipment, and fluorescence data acquisition will also ideally be provided. Control will generally be enhanced by improved techniques for more accurate reading of current and voltage, including the use of high read out rates. A wide variety of data system architectures might be used with station 103, for example, use of alternative analog to digital converter arrangements for handling of data acquisition.

In addition to the software enhancements for handling multiplexed microfluidic devices and systems, additional software modules might be implemented to provide real time data processing (e.g., signal processing algorithms might be run to identify regions of interest or to quantify fluorescence intensities or peak areas in regions of interest, correlate quantitative data with a particular sample within the multiwell plate, to calculate percent of inhibition provided by a sample, and/or provide positive controls of the assay). Real time voltage and/or current sensing and feedback might be used to actively control flow rates, timing of injection into high salt plugs, and the like. Advanced error handling protocols might also be available in real time to, for example, allow continuous monitoring of current to detect blockage of fluid flow within the microfluidic network, allow continuous monitoring of data for positive controls included in the experimental set-up so that the operator can be alerted if the data fall outside of a specified range, or the like. The format of data input and/or output files will preferably be compatible with commercially available database software packages.

Figure 9:
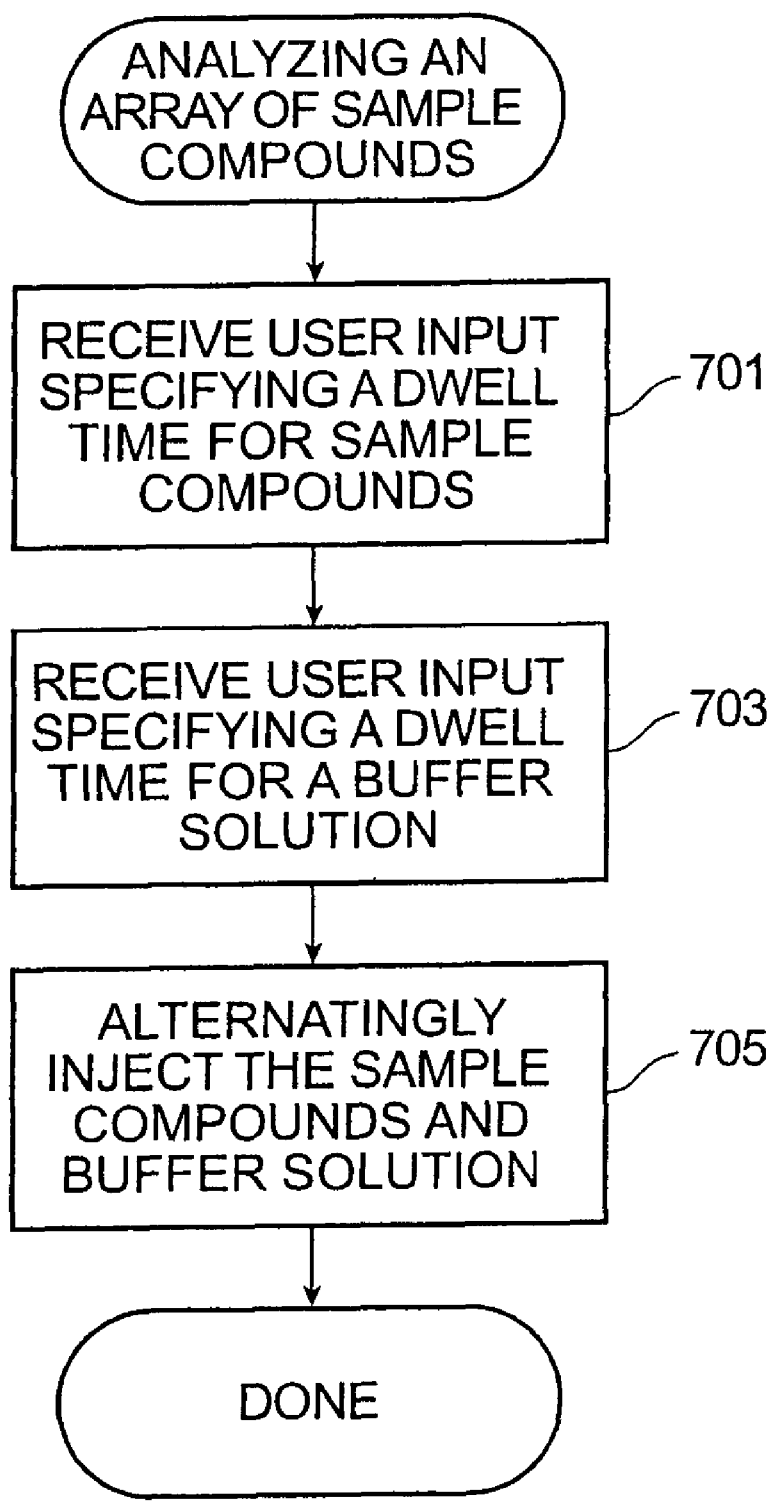
FIG. 9 shows a flowchart of a process of analyzing an array of sample compounds utilizing a high throughput microfluidic device.

FIG. 9 shows a flowchart of a process of analyzing an array of sample compounds that can be utilized with the high throughput microfluidic system described herein. At a step 701, user input specifying a dwell time for sample compounds is received. User input specifying a dwell time for a buffer solution can be received at a step 703. In preferred embodiments, the user input is entered using a graphical user interface. Once the dwell times for the sample compounds and buffer solution are received, the dwell times are sent to high throughput screening station 103 to alternatingly injection the sample compounds and buffer solution with the specified dwell times at a step 705.

Typically, the operation of the high throughput screening station is directed by a script of commands. In order to assist the user in generating the script, the invention provides graphical user interfaces for the user to specify characteristics of the script. Additionally graphical user interfaces can be utilized to control the execution of the script while it is processing sample compounds in the multiwell plates.

Figure 10A:
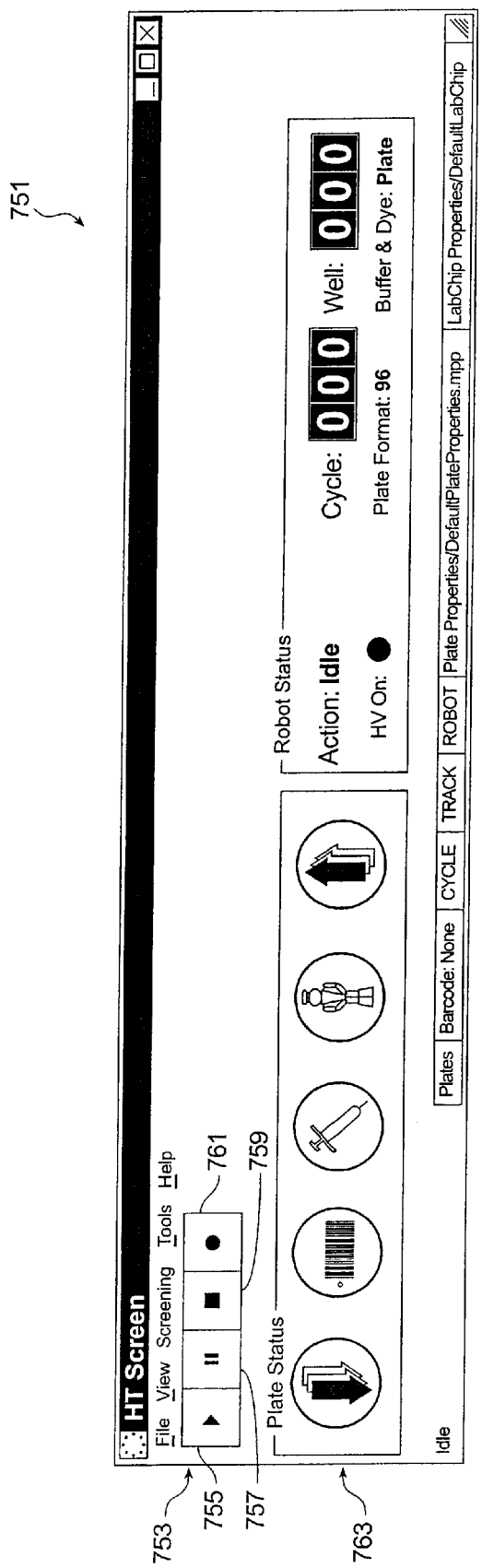
FIGS. 10A–10I show examples of windows that can be displayed on a computer system to assist the user in directing the operation of the high throughput microfluidic system.
Figure 10B:
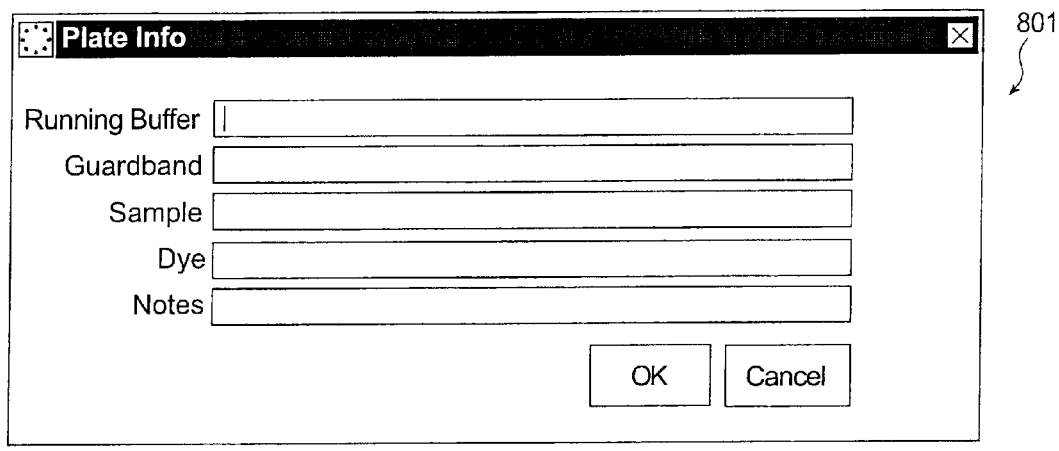

FIG. 10A shows a window 751 that can be utilized to set and modify characteristics of the script and control operation of the script in progress. Windows 751 includes a button bar 753 that includes a play button 755, a pause button 757, a stop button 759, and a reset button 761. Start button 755 will start the script and therefore the operation of the high throughput screening station. Typically, plates will be translated from input stack 109 by conveyor system 107 to bar code reader 15, dilution station 117, test station 119, and output stack 111. Screening may continue until the screening station runs out of plates in input stacker 109. If a recycle option is turned on in the plate properties, then all the plates will be re-stacked from the output stack to the input stack and the screening process can continue.

Pause button 757 pauses the screening by freezing the state machine and pausing the script. When the script is paused, it will not go to the next execution line. Instead, the screening station will wait until play button 755 is pressed. Preferably, the translation of the plates is stopped at convenient locations such as at bar code reader 115, dilution station 117 or test station 119.

Stop button 759 will stop the operation of this screening station. The translation of the plates will cease and should a user wish to continue, reset button 761 can be utilized to reset the screening station so that it can continue by activating play button 755.

Reset button 761 will cause the screening station to clear all the plates from path 113 by translating them towards the output stacker. Additionally, the robot will be directed to return to a home position. The actions available through button bar 753 are also available through pull down menus in window 751.

A pull down menu from window 751 will cause window 801 to be displayed. Window 801 allows the user to enter information regarding the plate. For example, the user can enter information regarding the buffer, guardband, sample, dye, and any notes that the user may feel would be helpful. The information can be stored in a database for later use. Another pull down menu allows the user to enter parameters for the operation of the high throughput screening station as follows.

Figure 10C:
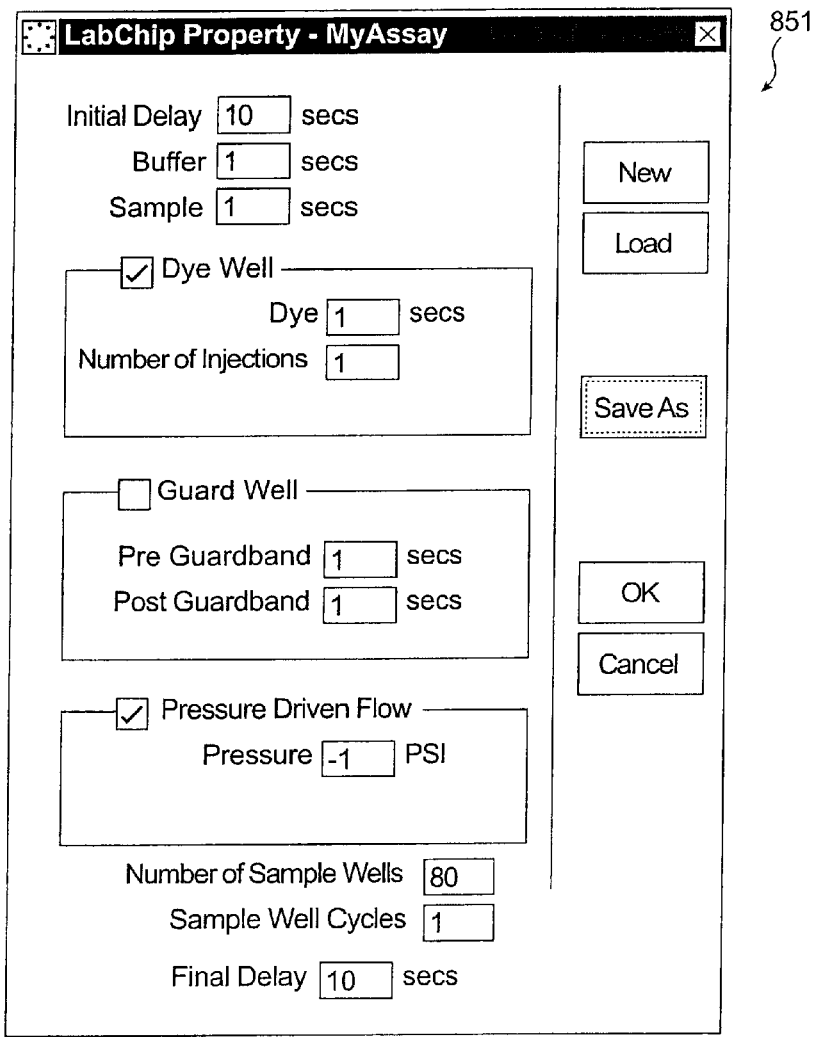

FIG. 10C shows a window 851 that the user can use to enter parameters for the operation of the screening station. As shown, the user can input an initial delay time before the sample compounds and buffer solution are injected into the microfluidic device. Additionally, user can input a final delay time that the screening station will delay after the sample compounds and buffer solution are injected into the microfluidic device.

Through window 851, a user can input a dwell time or the buffer solution as well as a dwell time for the sample compound. In one embodiment, the first column of wells on the plate are for the buffer solution. In general, the sample compounds and buffer solution will be alternatingly injected into the microfluidic device for the specified dwell times. Other fluids, such as those including dyes or guard fluids, can also be injected as follows.

In some applications, it is desirable to inject a dye into the microfluidic device, such as to mark sample compounds. A user can indicate that there are dye wells on the plate utilizing window 851. Additionally, the user can specify a dwell time for the dye and the number of injections for the dye. In one embodiment, the dye injections are performed before the sample compounds are injected into the microfluidic device and after each row of sample compounds in the plate. The dye can be stored in the second column of the microwell plate or any other location.

In some applications, it is desirable to inject guard fluids before and after each sample compound is injected. The guard fluids can be utilized to isolate and/or identify each of the multiple sample compounds. If a user indicates that the guardwell should be used, a pre guardband fluid will be injected for the specified dwell time and a post guardband fluid will be injected after the sample compound for the specified dwell time. In one embodiment, guard fluids are stored in second column of the plate, but can be placed in any location. For example, a guard fluid can be store off the plate in a trough. Utilizing an off plate trough for a guard fluid (or dye, buffer or other fluid) allows more or all of the wells on a plate to hold sample fluids.

A user can specify the pressure that should be utilized to drive the sample compounds and buffer solution through the microfluidic device in window 851. As shown, the pressure is specified in pounds per square inch, but other measurements for pressure can be utilized. The pressure can be generated by pressure at one or more of the wells, vacuum at one or more of the wells, vacuum at a waste well, or any combination of these. The user can also enter in window 851 the number of sample compound injections that are to be performed on each plate, not including the buffer solution, dye or guardfluids, if any. The sample well cycles indicate the number of times the same plate needs to be screened before going onto the next plate.

Figure 10D:
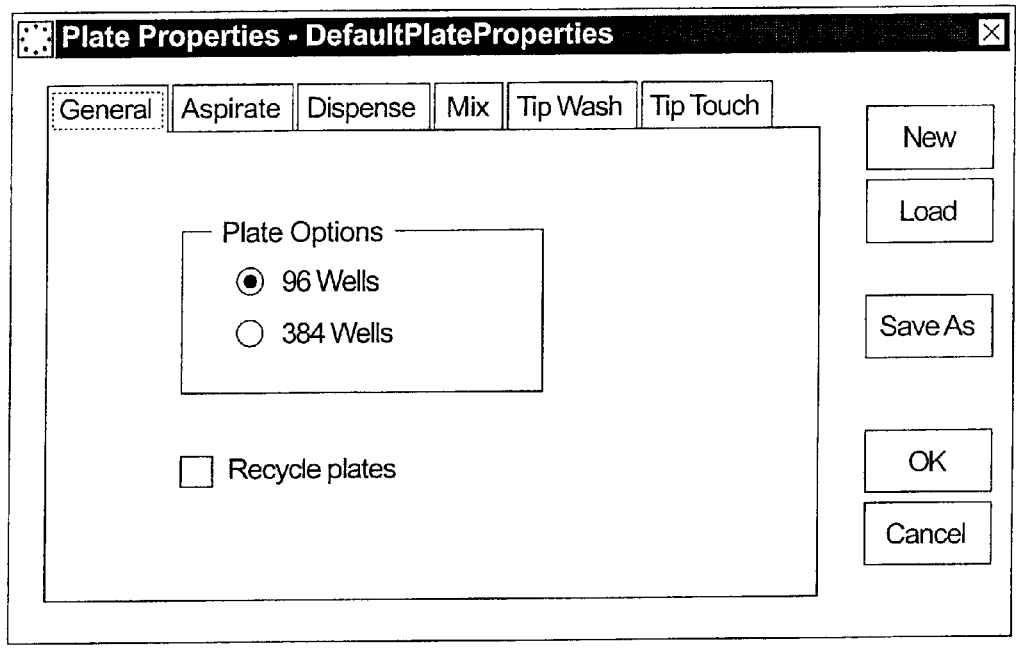

FIGS. 10D–10I show windows that can be utilized to specify other plate properties. In FIG. 10D, a user is able to specify the number of wells on the plate utilizing a window 881. Additionally, the user can specify that the plate should be recycled, which indicates that after the plates are screened they should be translated form the output stack to the input stack so that screening can continue.

Figure 10E:
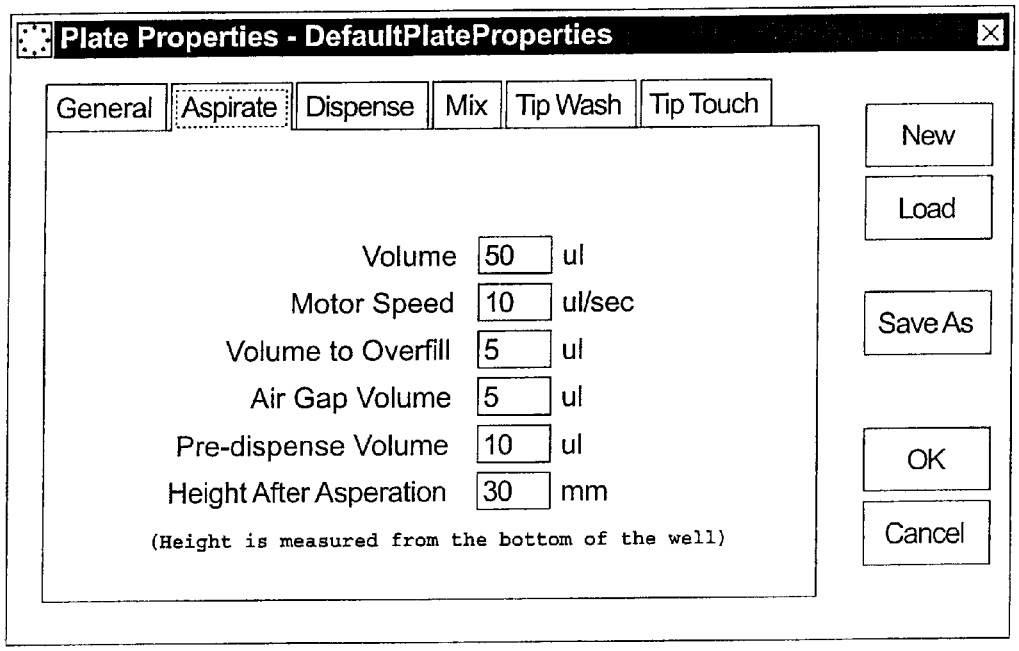

A window 901 in FIG. 10E allows the user to enter aspiration options for the dispense head. As shown, a user can enter the volume, motor speed, volume to overfill, air gap volume, pre-dispense volume, and height after aspiration. The motor speed indicates the speed at which aspiration is to progress and the volume to overfill (also known as the carry volume), which is an extra aspirate volume which will be retained in the tip and made unavailable for dispensing. Accordingly, the volume to overfill is eliminated at the beginning of a new aspirate operation. The air gap volume (also known as the blow-out) is the volume of air that will be utilized to "blow-out" the residual fluid in the tip following a dispense command. The pre-dispense volume will be dispensed immediately after the aspiration at the aspiration height and the height after aspiration indicates the height of the tip after the aspiration function.

Figure 10F:
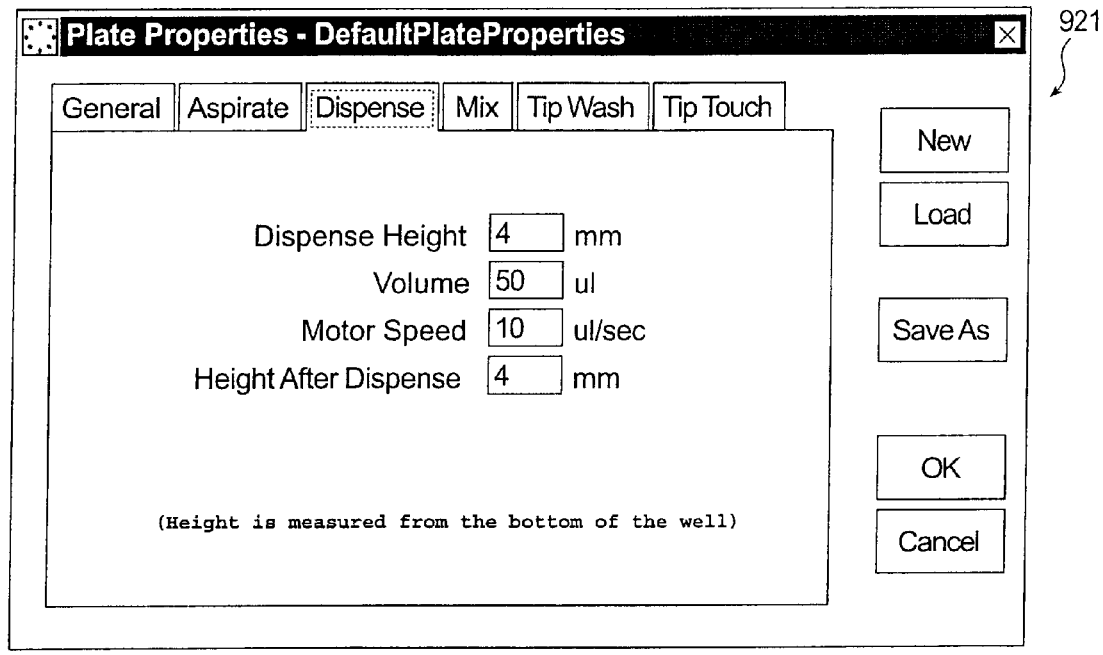

In FIG. 10F, a window 921 allows dispense parameters to be entered including the dispense height, volume, motor speed, and height after dispense. The dispense height indicates the height where the liquid needs to be dispensed. The volume and motor speed indicate how the liquid should be dispensed and the height after dispense indicates the height where the dispense head should go after the dispense function.

Figure 10G:
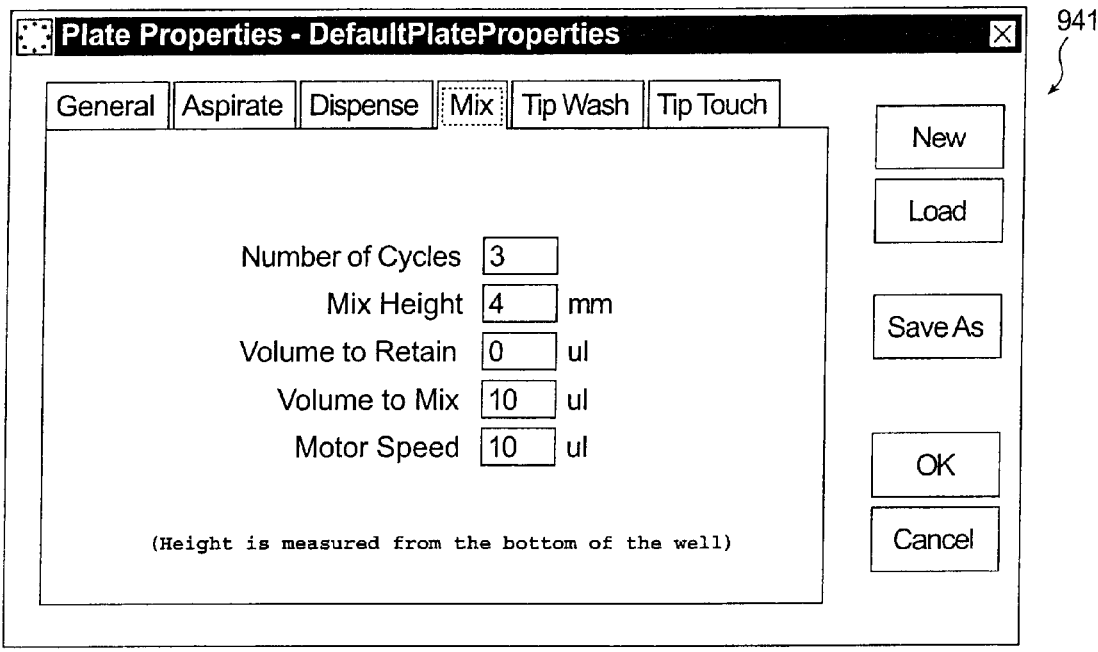

A window 941 in FIG. 10G allows mix parameters to be entered by the user. The mix parameters include the number of cycles, mix height, volume to retain, volume to mix, and motor speed. The number of cycles indicates the number of mixing cycles to occur during the mix function and the height indicates where the mix action should occur. The volume to retain is the volume of fluid to be retained after the final mix cycle. The volume to mix indicates the volume to be used to perform each mix cycle and the motor speed indicates the speed at which the mix function should progress.

Figure 10H:
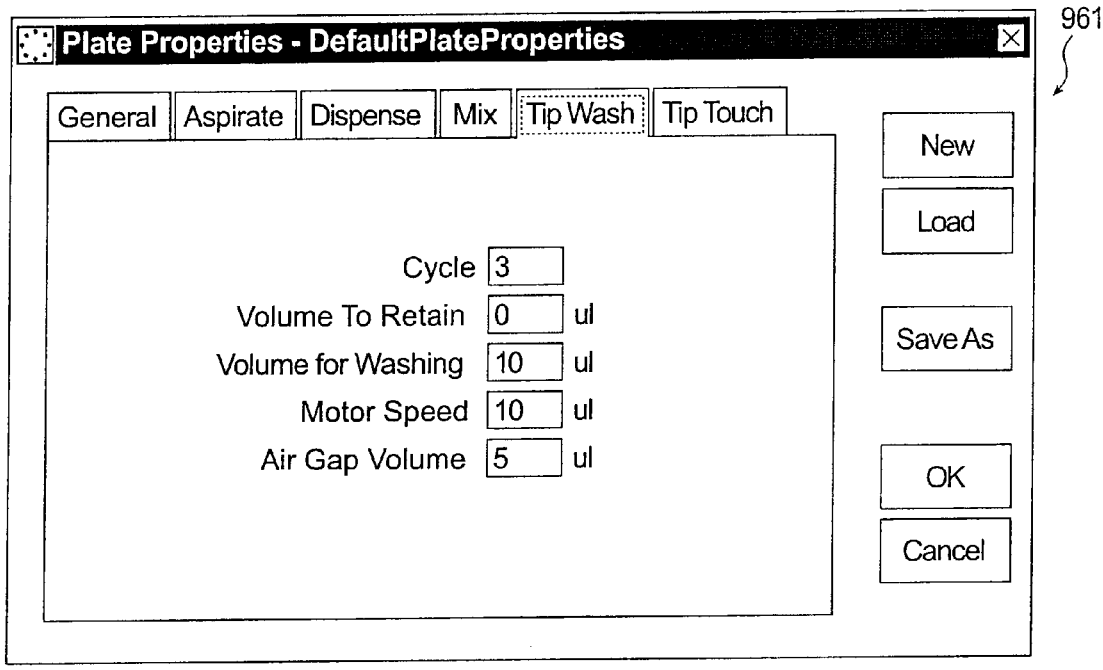

In FIG. 10H, a window 961 allows a user to input tip wash parameters. The tip wash parameters include the cycle, volume to retain, volume for washing, motor speed, and air gap volume. The cycle indicates the number cycles to occur during the tip wash function and the volume to retain indicates the amount of fluid to obtain after the final tip wash cycle. The volume for washing is the volume to use for washing the tips and the motor speed indicates the speed at which the washing should progress. Lastly, the air gap volume is the volume of air to be aspirated into the pipette tips before the start of the tip wash cycle. This air will be expelled at the end of the cycle to purge the tips of any residual fluid.

Figure 10I:
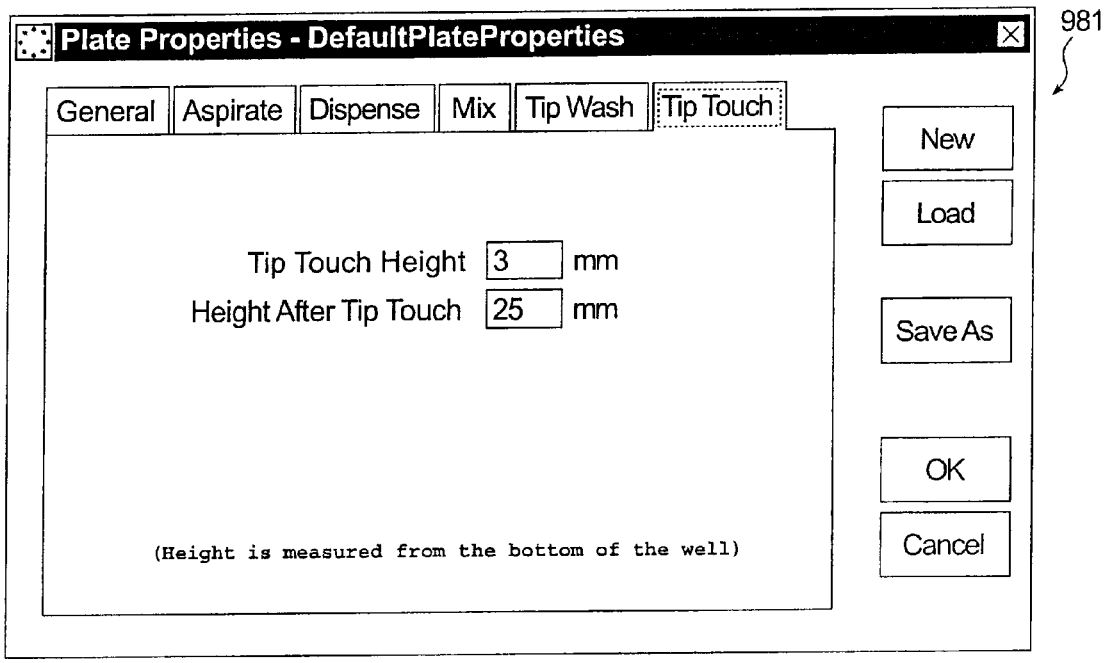

A window 981 in FIG. 10I allows a user to enter tip touch parameters including tip touch height and height after tip touch. The tip touch height is the height where the tip touch operation should begin and the height after tip touch is the height where the dispense head should go after performing the tip touch function.

Figure 11:
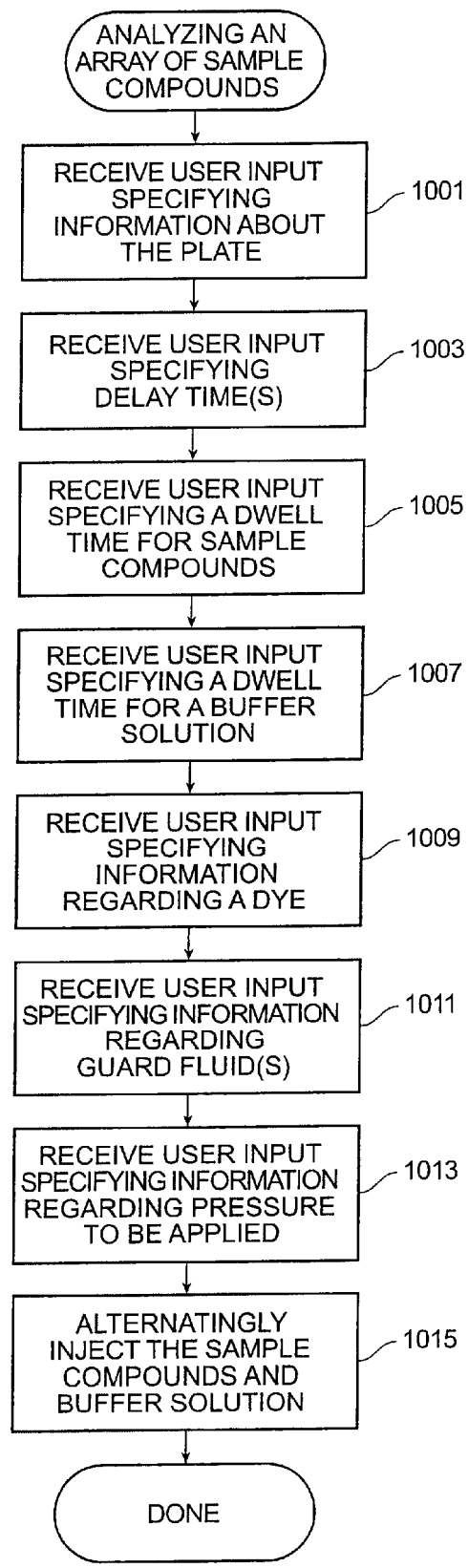
FIG. 11 shows a flowchart of another process of analyzing an array of sample compounds with the high throughput microfluidic system.

As can be seen by the figures, the user is able to enter various parameters for controlling the operation of the high throughput screening station. FIG. 11 shows a flowchart of a process of analyzing an array of sample compounds. At a step 1001 user input specifying information about the plate is received. The information received can be as shown in FIG. 10D. At a step 1003, user input specifying delay times is received. The delay times can be entered as shown in FIG. 10C and can include one or more of an initial delay or a final delay.

User input specifying a dwell time for sample compounds is received at a step 1005 and user input specifying a dwell time for a buffer solution is received at a step 1007. The dwell times can be entered as shown in FIG. 10C.

At a step 1009, user input specifying information regarding a dye can be received. The information can be whether to utilize a dye well or fluid and can additionally include a dwell time and number of injections as shown in FIG. 10C. User input specifying information regarding one or more guard fluids is received at a step 1011. The guard fluid information can include dwell times for one or more of a pre or post guardband fluid.

User input specifying information regarding pressure to be applied can be received at a step 1013. The pressure specified can be the pressure to drive fluids through the microfluidic device and can be entered as shown in FIG. 10C.

At a step 1015, the sample compounds and buffer solution are alternatingly injected into the microfluidic device. The operation of the screening station will be as specified by the parameters the user has entered. Although the flowchart in FIG. 11 shows a specific order of step for convenience, the steps can be performed in various orders and steps can be added, deleted, combined, and modified within the scope of the invention.

Figure 12:
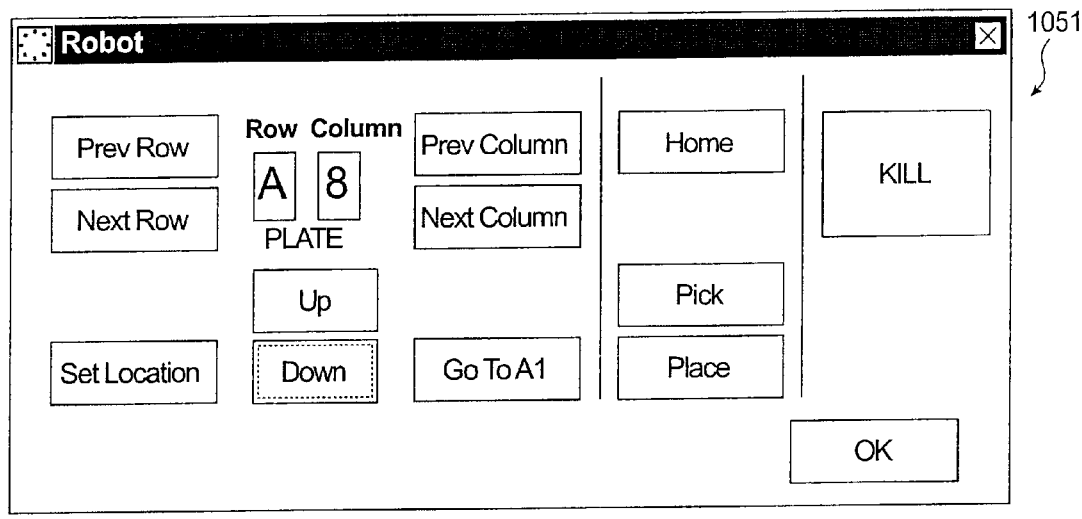
FIG. 12 shows an example of a window or graphical user interface that can be utilized to ascertain and set parameters for a robot within the system.

FIG. 12 shows a window 1051 that allows the user to move the robot (and plate if it is being held by the robot) to a specified position. Additionally, menus can be provided that allow the user to configure the robot by teaching it positions and configuring specific X, Y, and Z coordinates for the plate.

In at least one aspect, the invention provides software that analyzes the data received from a microfluidic laboratory system. For example, in the case of pharmaceutical applications, the software typically analyzes the data and identifies from that data, any samples or test compounds that potentially have an effect on the screening assay that is being run. In preferred aspects, continuous flow assay methods are utilized which rely upon a continuous stream of assay reagents along a main analysis channel in the microfluidic device. These assay methods are described in U.S. Pat. No. 5,942,443, previously incorporated by reference. Other methods are described in U.S. application Ser. No. 09/338, 239, filed Jun. 22, 1999 and Published PCT Application WO 99/64840, which are both hereby incorporated by reference.

The assay reagents are selected to produce a steady state or otherwise regular or predictable signal intensity within the analysis channel. For example, in a fluorogenic enzyme assay, enzyme and fluorogenic substrate are flowed along the analysis channel wherein they produce a steady level of fluorescent product that is indicative of the normal activity of the enzyme upon the substrate under the particular conditions. The fluorescent signal is monitored at a detection zone within the main channel. Periodically, test materials or sample compounds are introduced into the main analysis channel to interact with the assay reagents, e.g., the enzyme and substrate. Where the sample compound inhibits or enhances the reaction with the analysis channel, it will lead to a decrease or increase in the level of signal, respectively, yielding a deviation in the regular signal intensity for the assay system.

As used herein, the term "regular signal" is indicative of a signal produced by assay reagents that has a relatively constant pattern when operating in control mode. This regular signal may take the form of a constant steady state signal reflective of a constant level of fluorescence, etc. from a fluorogenic assay, or alternatively, may include regular signal peaks and valleys reflective of separated products and substrates for nonfluorogenic assay formats, e.g., where fluorescent products are separated from fluorescent substrates. Where a sample compound has an effect on the assay being performed, it will result in a deviation in signal from these regular peaks and valleys, depending upon whether the compound is an inhibitor or an enhancer. These nonfluorogenic assays are described in detail in U.S. Pat. No. 5,942,443, and in U.S. patent application Ser. No. 09/093,489, filed Jun. 8, 1998, each of which is incorporated by reference.

The software generally provides for the receipt of the raw signal data from a detector disposed in sensory communication with the analysis channel (e.g., adjacent to and positioned to measure the signal from the channel). The software then analyzes the regular signal, identifies any deviations in that regular signal, and identifies the particular sample compound that yielded that effect, e.g., position in a multiwell plate from which the compound was drawn.

Figure 13:
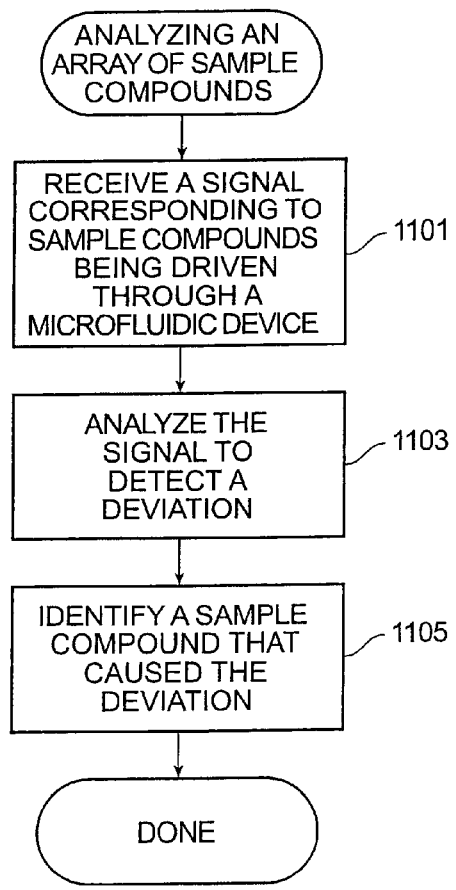
FIG. 13 shows a flowchart of a process of analyzing an array of sample compounds by detecting a deviation in a signal and identifying the sample compound that caused the deviation.

FIG. 13 shows a flowchart of a process of analyzing an array of sample compounds to identify a sample compound that caused an effect on the reaction. At a step 1101, a signal corresponding to sample compounds being driven through a microfluidic device is received. In some fluorogenic applications, the signal will evidence a steady state and sample compounds can cause an effect on the signal (e.g., either a higher or lower signal than expected).

At a step 1103, the signal is analyzed to detect a deviation. It is expected that the deviation is a result of the sample compound's effect on the reaction. A deviation can be detected if the signal exceeds a threshold deviation, such as by a percentage of the expected signal. The sample compound that caused the deviation is identified at a step 1105.

In analyzing the data from the analysis channel, the software typically establishes or identifies a signal profile that is indicative of the "regular signal" (e.g., steady state signal) referenced above. This is often accomplished by initially running a series of negative control experiments through the system. As the assay progresses, the data is compared against the control or expected signal profile. When a deviation is detected by the computer, it is compared to a threshold deviation level to determine if the deviation is a "hit." The threshold level may be preselected, e.g., by the programmer or the user, to account for normal levels in signal deviation, filter out less active hits, or the like. Typically, the threshold identifies a "hit" deviation as some fraction of the expected signal level at a given point in the signal profile. For example, where a signal drops or increases by 10% or more of the expected signal level, it may be identified as a hit. The actual percentage level may be adjusted depending upon the factors described above, e.g., 20%, 30%, 40%, 50%, or up to 100% variation in the signal over the regular or expected signal level. Although described as percentages of signal, the actual threshold deviation may be set in terms of a variety of factors, e.g., fluorescent intensity units, standard deviations, etc.

Figure 14A:
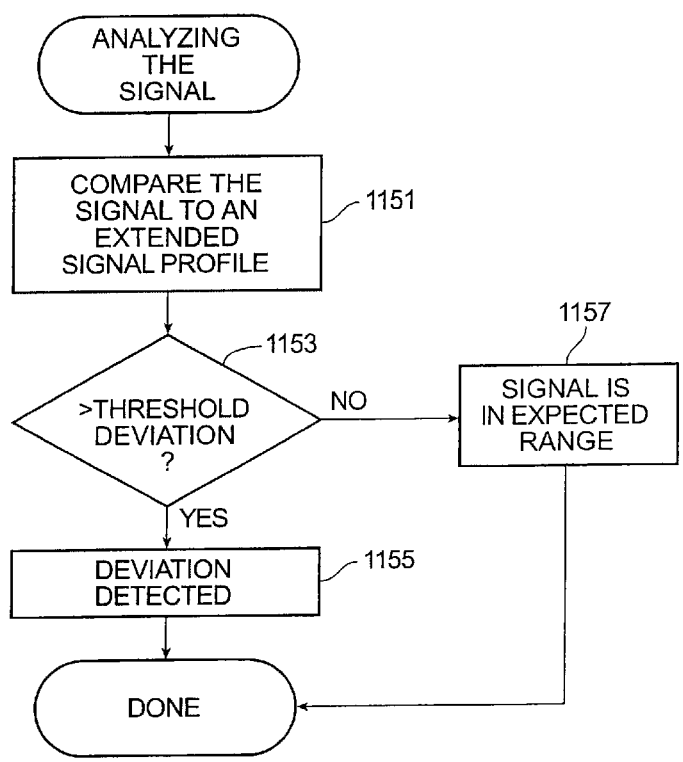
FIG. 14A shows a flowchart of a process of analyzing the signal to detect a deviation and FIGS. 14B and 14C show examples of plots to illustrate an expected signal profile and detected deviations.

FIG. 14A shows a flowchart of a process of analyzing the signal to detect a deviation. At a step 1151, the signal is compared to an expected signal profile. If the signal is found to be greater than a threshold deviation at a step 1153, a deviation is detected at a step 1155. Otherwise, the signal is found to be in an expected range at a step 1157.

Figure 14B:
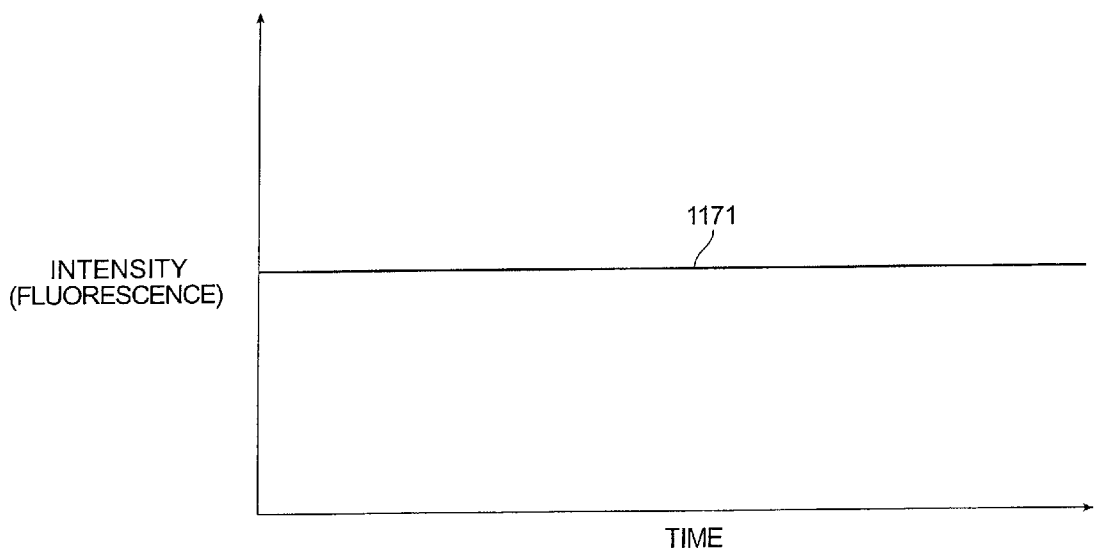
Figure 14C:
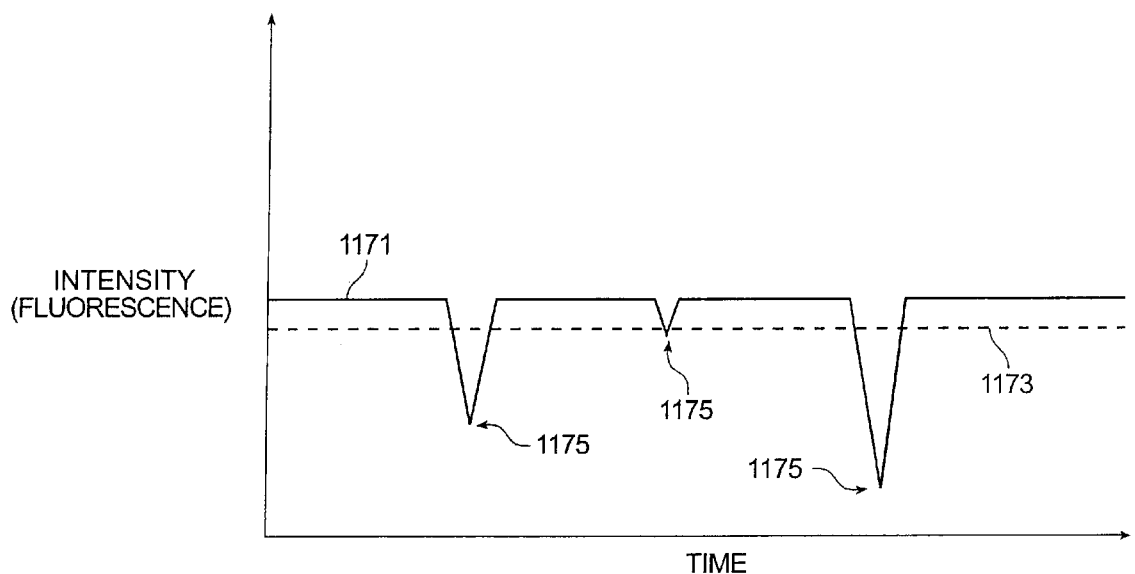

An expected signal profile may be a steady state signal as illustrated in FIG. 14B. As shown, a steady state signal 1171 represents a relatively constant fluorescent intensity over time. FIG. 14B shows that a threshold 1173 can be utilized to detect a deviation or hit, which may be characteristic of a reaction of interest. As shown, there are three deviations 1175 in intensity that cross threshold 1173. As mentioned above, the threshold can also be represented as a percentage of the expected signal. Additionally, depending on the experiment, the deviation may be defined in terms of a decrease (or increase) in signal intensity followed by an increase (or decrease) in signal intensity.

Typically, periodic wells within a library plate, e.g., a 96, 384 or 1536 well plate, will be spiked with a measurable amount of a detectable compound as a position marker. For example, every tenth, twelfth, or the like, well is spiked with the marker compound. This is often accomplished by spiking all of the wells in a given column or row of wells in a given plate. These position markers are detected by the detector as they flow through the analysis channel of the microfluidic device and counted by the computer to provide an indication of the particular well of the plate being assayed at any given time. Typically, these markers are distinguishable from the signal produced by the assay reagents, e.g., having a different fluorescent excitation or emission maximum. Appropriate optics within the detection system allow for separate detection of these markers and the assay signals.

Typically, the software monitors, e.g., counts the number or markers that have been detected for a given plate or series of plates. When the software identifies a deviation in the regular signal from the assay reagents, e.g., a "hit," it then determines the position of the compound in terms of the number of markers that came before the hit, and calculates the position or well in the plate from which the compound was drawn. The software can then instruct the system to re-assay sample compounds in the identified well, wells on either side or otherwise adjacent to the identified well, and/or wells corresponding to the signal near the identified well. This re-assaying can be utilized to verify the accuracy of the experimental results, such as, for example, to ensure that the deviation was not the result of neighboring wells. Alternatively or additionally, the software can produce a display of the well or wells that yielded potential hits, for the investigator to use in subsequent analyses.

Figure 15:
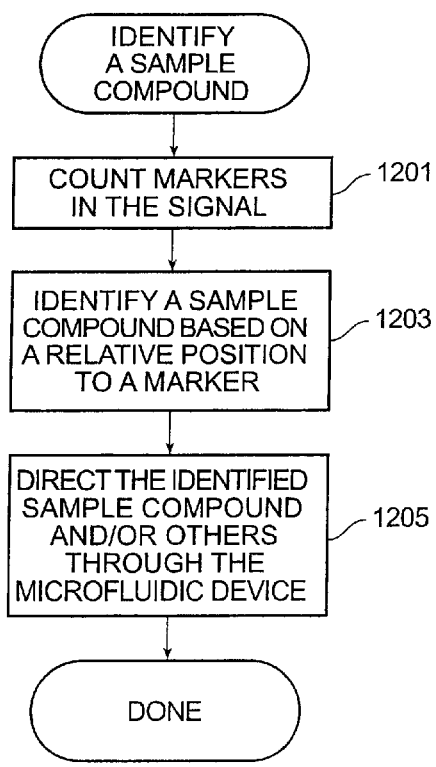
FIG. 15 shows a flowchart of a process of identifying a sample compound based on a relative position of a marker and verifying the results.

FIG. 15 shows a flowchart of a process of identifying a sample compound. At a step 1201, markers are counted in the signal. The use of markers is optional but it may make it easier in some application to identify the sample compounds that are responsible for a deviation or effect on the reaction. The sample compound is identified based on its relative position to a marker at a step 1203. Thus, the markers all more accurate identification of the sample compound that caused a deviation.

At a step 1205, the identified sample compound and/or other sample compounds are directed through the microfluidic device for further analysis. In order to increase the accuracy of the results, the identified sample compound can be re-assayed, preferably surrounded in the signal by different sample compounds so that it can be verified if the deviation was the result of the identified sample compounds. Thus, in an application where the wells are sampled sequentially, wells that are near the well of the sample compound can be utilized that were not near the identified sample compound in the signal in the first assay.

Figure 16:
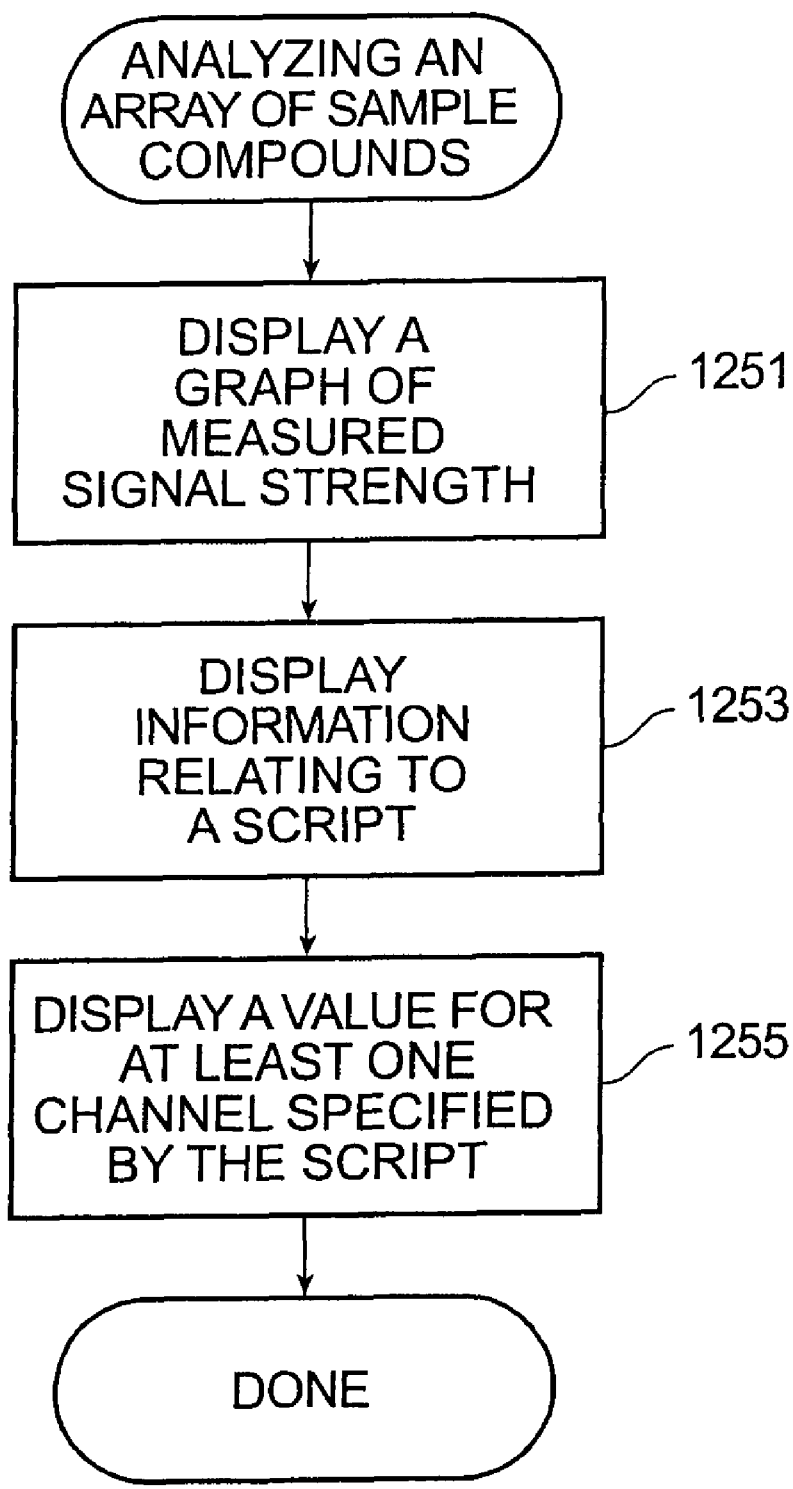
FIG. 16 shows a flowchart of a process of analyzing an array of sample compounds by displaying information from the operation of the high throughput microfluidic system.

As described above, graphical user interfaces for directing the operation of the high throughput screening station can be utilized. Graphical user interfaces can also be utilized to analyze data that is received from the screening station. FIG. 16 shows a flowchart of a process of analyzing an array of compounds where data from a screening station is displayed.

At a step 1251, a graph of measured signal strength is displayed. The signal strength can be a fluorescent measurement from the detection point of the microfluidic device. As mentioned previously, a script can be utilized to direct the operation of the screening station and information relating to the script can be displayed at a step 1253.

Figure 17A:
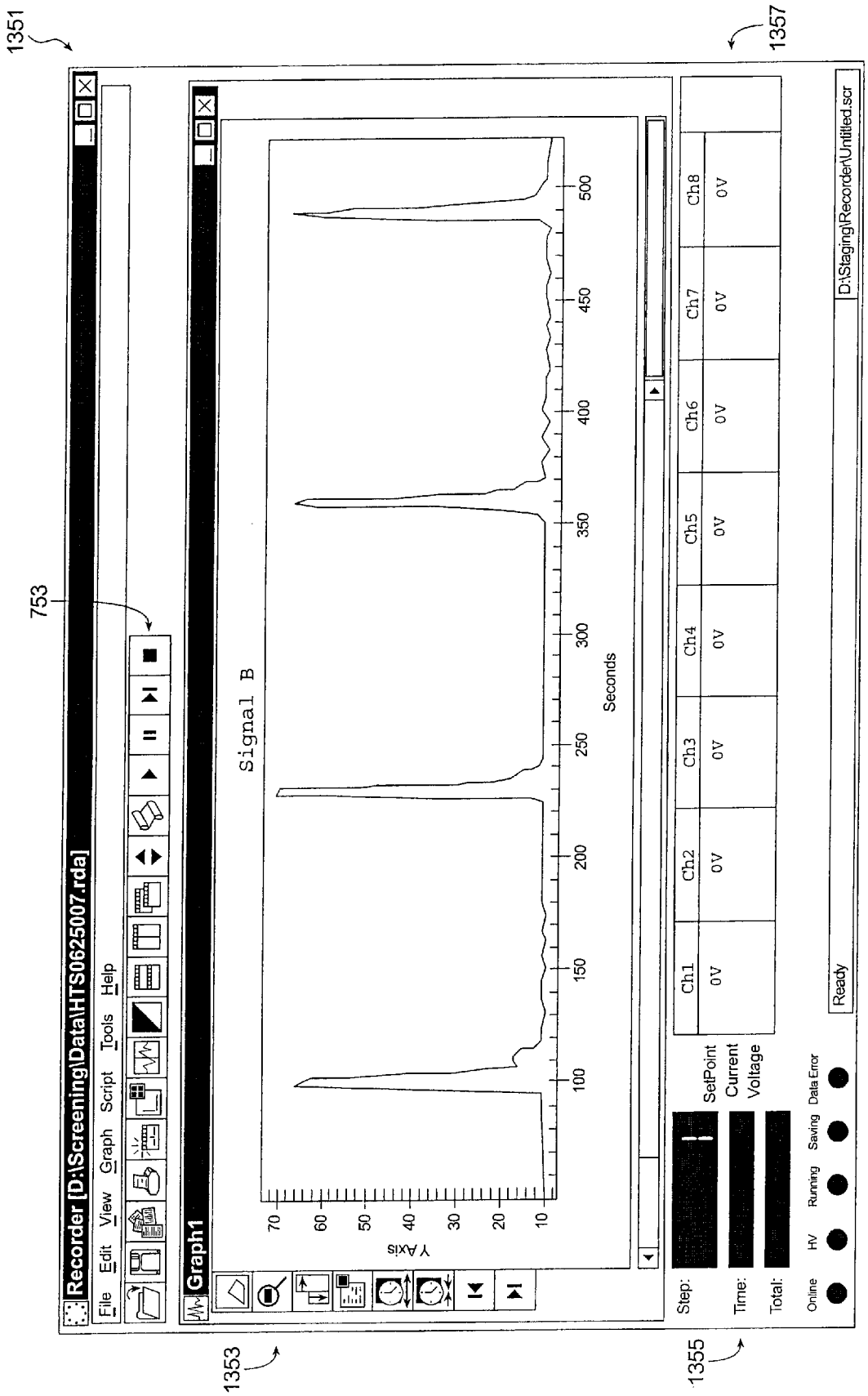

At a step 1255, a value for at least one channel specified by the script can be displayed. FIG. 17A shows a window 1351 that displays the information described in reference to the flowchart of FIG. 16. Within window 1351 is button bar 753 that operates similar to as was described in reference to FIG. 10A. Additionally, a sub window 1353 includes a graph of the measured signal strength as the sample compounds flow past a detection point of the microfluidic device. The signal strength is graphed over time as shown.

Window 1351 also includes information 1355 regarding the script that is currently directing the operation of the screening station including the step number, time of operation for this step and the total time of operation. In an area 1357 of window 1351, parameters for at least one channel are displayed. The parameters can include the set point, current and/or voltage.

Figures 17B, 17C:
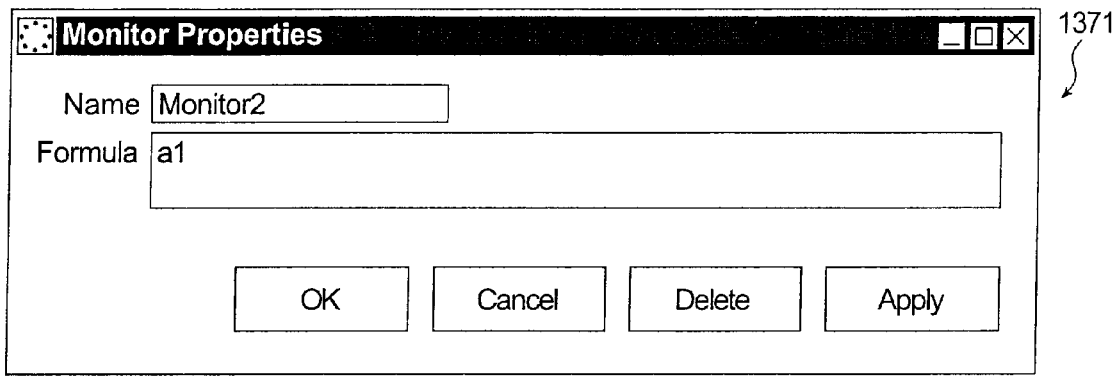

In one aspect of the invention, a user is able to enter a formula that will be calculated and displayed on the screen, typically in area 1357 of window 1351. In FIG. 17B, a window 1371 allows a user to enter a formula to be calculated and displayed. The formula can utilize the operators that are shown in a table 1391 of FIG. 17C and predefined functions that are shown in a table 1395 of FIG. 17D.

Figure 17E:
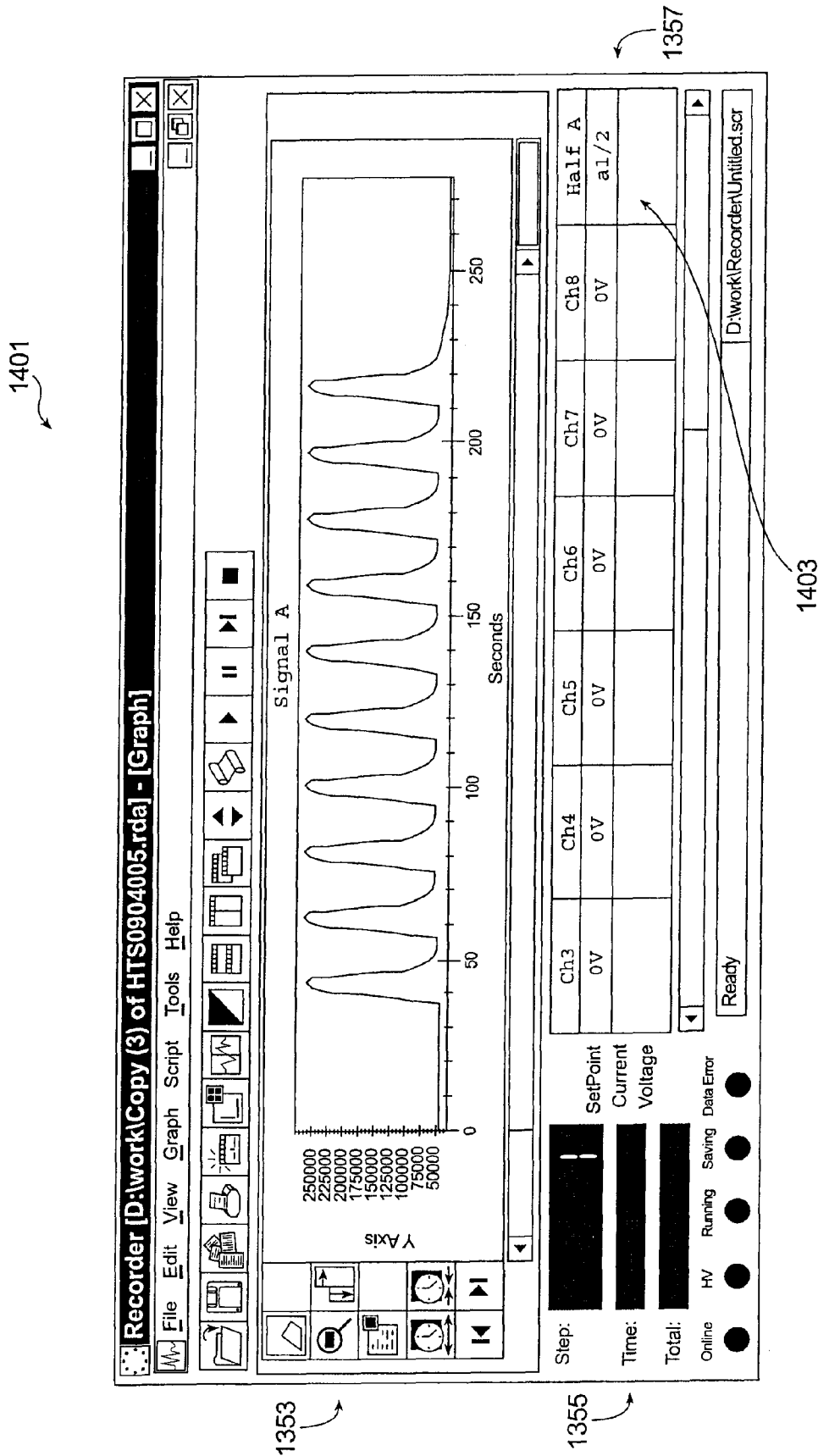

Once a user has entered a formula, the computer system calculates the value of the formula and displays it on the screen. For example, FIG. 17E shows a window 1401 that shows a formula that is half the value of A1. As shown, the result of the formula is calculated and displayed at a location 1403, adjacent to the display of channel parameters.

The invention has now been explained with reference to specific embodiments. Other embodiments will be apparent to those of ordinary skill in the art in view of the foregoing description. For example, the invention can be advantageously applied to other high throughput microfluidic systems and applications in addition to those described herein. It is therefore not intended that this invention be limited expect as indicated by the appended claims along with their full scope of equivalents.

What is claimed is:

1. A computer implemented method of analyzing an array of sample compounds utilizing a microfluidic device, comprising:
   receiving a signal corresponding to sample compounds being driven through the microfluidic device;
   analyzing the signal to detect a deviation from a steady state signal, wherein analyzing the signal includes determining if the signal exceeds a threshold deviation, wherein the threshold deviation is 10%; and
   identifying a sample compound that caused the threshold deviation.

2. A computer implemented method of analyzing an array of sample compounds utilizing a microfluidic device, comprising:
   receiving a signal corresponding to sample compounds being driven through the microfluidic device;
   analyzing the signal to detect a deviation from a steady state signal, wherein analyzing the signal includes determining if the signal exceeds a threshold deviation and wherein the expected signal profile is based on a signal from a control experiment for obtaining the expected signal profile; and
   identifying a sample compound that caused the threshold deviation.

3. A computer implemented method of analyzing an array of sample compounds utilizing a microfluidic device, comprising:
   receiving a signal corresponding to sample compounds being driven through the microfluidic device, wherein the sample compounds are stored in multiple wells in which markers are stored in known wells;
   analyzing the signal to detect a deviation from a steady state signal, wherein analyzing the signal includes determining if the signal exceeds a threshold deviation; and
   identifying a sample compound that caused the threshold deviation.

4. The computer implemented method of claim 3, wherein the markers are stored at regular well intervals.

5. The computer implemented method of claim 3, wherein identifying a sample compound includes determining relative position of the well of the sample compound in relation to a well of a marker.

6. A computer implemented method of analyzing an array of sample compounds utilizing a microfluidic device, comprising:
   receiving a signal corresponding to sample compounds being driven through the microfluidic device;
   analyzing the signal to detect a deviation from a steady state signal, wherein analyzing the signal includes determining if the signal exceeds a threshold deviation;
   identifying a sample compound that caused the threshold deviation;
   identifying sample compounds in the signal that are near in time being driven through the microfluidic device to the identified sample compound; and
   directing the identified sample compounds to be driven through the microfluidic device again for analysis.

7. A computer implemented method of analyzing an array of sample compounds utilizing a microfluidic device, comprising:
   receiving user input specifying a dwell time for the sample compounds;

receiving user input specifying a dwell time for a buffer solution;

receiving user input specifying at least one of an initial delay time before the sample compounds and buffer solution are injected into the microfluidic device and a final delay time after the sample compounds and buffer solution are injected into the microfluidic device; and alternatingly injecting the sample compounds and buffer solution into the microfluidic device for the specified dwell times for the sample compounds and buffer solution.

8. The computer implemented method of claim 7, further comprising receiving user input specifying that a dye be injected into the microfluidic device before the sample compounds.

9. The computer implemented method of claim 8, further comprising receiving user input specifying a dwell time for the dye.

10. The computer implemented method of claim 8, further comprising receiving user input specifying a number of injections for the dye.

11. The computer implemented method of claim 7, further comprising receiving user input specifying that guard fluid should be injected into the microfluidic device before and after each of the sample compounds.

12. The computer implemented method of claim 11, further comprising receiving user input specifying a dwell time for the guard fluid.

13. The computer implemented method of claim 11, further comprising receiving user input specifying a first dwell time for the guard fluid before each of the sample compounds is injected and a second dwell time for the guard fluid after each of the sample compounds is injected.

14. The computer implemented method of claim 7, further comprising receiving user input specifying that pressure should be utilized to drive the sample compounds and buffer solution through the microfluidic device.

15. The computer implemented method of claim 14, further comprising receiving user input specifying a pressure to be applied to the sample compounds and buffer solution.

16. The computer implemented method of claim 15, further comprising receiving user input specifying a number of wells for the sample compounds on the array.

17. The computer implemented method of claim 7, further comprising receiving user input specifying a number of times each sample compound should be analyzed.

18. The computer implemented method of claim 7, further comprising receiving user input specifying a number of wells on the array.

19. The computer implemented method of claim 7, wherein the microfluidic device includes at least two intersecting channels.

20. The computer implemented method of claim 7, wherein the microfluidic device includes at least two intersecting channels with a cross sectional dimension in a range of about 0.1 $\mu$m to about 500 $\mu$m.

21. A computer program product that analyzes an array of sample compounds utilizing a microfluidic device, comprising:

computer code that receives user input specifying a dwell time for the sample compounds;

computer code that receives user input specifying a dwell time for a buffer solution;

computer code that directs the sample compounds and buffer solution to be alternatingly injected into the microfluidic device for the specified dwell times for the sample compounds and buffer solution;

computer code that receives user input specifying at least one of an initial delay time before the sample compounds and buffer solution are injected into the microfluidic device and a final delay time after the sample compounds and buffer solution are injected into the microfluidic device; and a computer readable medium that stores the computer codes.

22. The computer program product of claim 21, wherein the computer readable medium is selected from the group consisting of CD-ROM, floppy disk, tape, flash memory, system memory, hard drive, and data signal embodied in a carrier wave.

23. The computer program product of claim 21, further comprising computer code that receives user input specifying that a dye be injected into the microfluidic device before the sample compounds.

24. The computer program product of claim 23, further comprising computer code that receives user input specifying a dwell time for the dye.

25. The computer program product of claim 23, further comprising computer code that receives user input specifying a number of injections for the dye.

26. The computer program product of claim 21, further comprising computer code that receives user input specifying that guard fluid should be injected into the microfluidic device before and after each of the sample compounds.

27. The computer program product of claim 26, further comprising computer code that receives user input specifying a dwell time for the guard fluid.

28. The computer program product of claim 26, further comprising computer code that receives user input specifying a first dwell time for the guard fluid before each of the sample compounds is injected and a second dwell time for the guard fluid after each of the sample compounds is injected.

29. The computer program product of claim 21, further comprising computer code that receives user input specifying that pressure should be utilized to drive the sample compounds and buffer solution through the microfluidic device.

30. The computer program product of claim 29, further comprising computer code that receives user input specifying a pressure to be applied to the sample compounds and buffer solution.

31. The computer program product of claim 30, further comprising computer code that receives user input specifying a number of wells for the sample compounds on the array.

32. The computer program product of claim 21, further comprising computer code that receives user input specifying a number of times each sample compound should be analyzed.

33. The computer program product of claim 21, further comprising computer code that receives user input specifying a number of wells on the array.

34. The computer program product of claim 21, wherein the microfluidic device includes at least two intersecting channels.

35. The computer program product of claim 21, wherein the microfluidic device includes at least two intersecting channels with a cross sectional dimension in a range of about 0.1 $\mu$m to about 500 $\mu$m.

36. A computer program product that analyzes an array of sample compounds utilizing a microfluidic device, comprising:

computer code that receives a signal corresponding to sample compounds being driven through the microfluidic device;

computer code that analyzes the signal to detect a deviation from a steady state signal, wherein the computer code that analyzes the signal includes computer code that determines if the signal exceeds a threshold deviation, wherein the threshold deviation is 10%;

computer code that identifies a sample compound that caused the threshold deviation; and a computer readable medium that stores the computer codes.

37. A computer program product that analyzes an array of sample compounds utilizing a microfluidic device, comprising:

computer code that receives a signal corresponding to sample compounds being driven through the microfluidic device;

computer code that analyzes the signal to detect a deviation from a steady state signal, wherein the computer code that analyzes the signal includes computer code that determines if the signal exceeds a threshold deviation and wherein the expected signal profile is based on a signal from a control experiment for obtaining the expected signal profile;

computer code that identifies a sample compound that caused the threshold deviation; and a computer readable medium that stores the computer codes.

38. A computer program product that analyzes an array of sample compounds utilizing a microfluidic device, comprising:

computer code that receives a signal corresponding to sample compounds being driven through the microfluidic device, wherein the sample compounds are stored in multiple wells in which markers are stored in known wells;

computer code that analyzes the signal to detect a deviation from a steady state signal, wherein the computer code that analyzes the signal includes computer code that determines if the signal exceeds a threshold deviation;

computer code that identifies a sample compound that caused the threshold deviation; and a computer readable medium that stores the computer codes.

39. The computer program product of claim 38, wherein the markers are stored at regular well intervals.

40. The computer program product of claim 38, wherein the computer code that identifies a sample compound includes computer code that determines relative position of the well of the sample compound in relation to a well of a marker.

41. A computer program product that analyzes an array of sample compounds utilizing a microfluidic device, comprising:

computer code that receives a signal corresponding to sample compounds being driven through the microfluidic device;

computer code that analyzes the signal to detect a deviation from a steady state signal, wherein the computer code that analyzes the signal includes computer code that determines if the signal exceeds a threshold deviation;

computer code that identifies a sample compound that caused the threshold deviation;

computer code that identifies sample compounds in the signal that are near in time being driven through the microfluidic device to the identified sample compound;

computer code that directs the identified sample compounds to be driven through the microfluidic device again for analysis; and a computer readable medium that stores the computer codes.

* * * * *